US011466261B2

(12) United States Patent
Chabriere et al.

(10) Patent No.: US 11,466,261 B2
(45) Date of Patent: Oct. 11, 2022

(54) MUTATED PTE ENZYMES

(71) Applicants: LA FONDATION MEDITERRANEE INFECTION, Marseilles (FR); I.N.S.E.R.M. (INSTITUT NATIONAL DE LA SANTÉ ET DE LA RECHERCHE MÉDICALE), Paris (FR); GENE AND GREEN TK, Marseilles (FR); ASSISTANCE PUBLIQUE-HOPITAUX DE MARSEILLE, Marseilles (FR); CENTRE NATIONAL DE LA RECHERCHE SCIENTIFIQUE, Paris (FR); AIX-MARSEILLE UNIVERSITE, Marseilles (FR)

(72) Inventors: Eric Chabriere, Marseilles (FR); David Daude, Marseilles (FR); Mikael Elias, Florange (FR)

(73) Assignees: LA FONDATION MEDITERRANEE INFECTION, Marseilles (FR); I.N.S.E.R.M. (INSTITUT NATIONAL DE LA SANTÉET DE LA RECHERCHE MÉDICALE), Paris (FR); GENE AND GREEN TK, Marseilles (FR); ASSISTANCE PUBLIQUE-HOPITAUX DE MARSEILLE, Marseilles (FR); CENTRE NATIONAL DE LA RECHERCHE SCIENTIFIQUE, Paris (FR); AIX-MARSEILLE UNIVERSITE, Marseilles (FR); REGENTS OF THE UNIVERSITY OF MINNESOTA, Minneapolis, MN (US)

(*) Notice: Subject to any disclaimer, the term of this patent is extended or adjusted under 35 U.S.C. 154(b) by 130 days.

(21) Appl. No.: 16/632,155

(22) PCT Filed: Jul. 17, 2018

(86) PCT No.: PCT/FR2018/051822
§ 371 (c)(1),
(2) Date: Jan. 17, 2020

(87) PCT Pub. No.: WO2019/016468
PCT Pub. Date: Jan. 24, 2019

(65) Prior Publication Data

US 2020/0231950 A1 Jul. 23, 2020

(30) Foreign Application Priority Data

Jul. 17, 2017 (FR) .................................... 17/56776

(51) Int. Cl.

| | |
|---|---|
| ***C12N 9/16*** | (2006.01) |
| ***A01N 63/50*** | (2020.01) |
| ***A61K 38/00*** | (2006.01) |

(52) U.S. Cl.
CPC ............... *C12N 9/16* (2013.01); *A01N 63/50* (2020.01); *C12Y 301/08001* (2013.01); *A61K 38/00* (2013.01)

(58) Field of Classification Search
None
See application file for complete search history.

(56) References Cited

U.S. PATENT DOCUMENTS 9,796,990 B2 * 10/2017 Scott ........................ A62D 3/02

FOREIGN PATENT DOCUMENTS

| | | |
|---|---|---|
| WO | WO2013/010225 | 1/2013 |
| WO | WO 2015/196106 | 12/2015 |
| WO | WO 2016/092555 | 6/2016 |

OTHER PUBLICATIONS

BLAST PDF of SEQ ID No. 1 (U.S. Appl. No. 16/632,155) vs. SEQ ID No. 2 (Scott et al. U.S. Pat. No. 9,796,990 B2) alignment. Printed PDF on Jan. 27, 2022 (Year: 2022).*
Written Opinion, PCT/FR2018/051822, dated Sep. 19, 2018.
International Search Report, PCT/FR2018/051822, dated Sep. 19, 2018.
French Search Report, FR 1756776, dated Jul. 2, 2018.
Cheng et al., "Purification and Properties of a Highly Active Organophosphorus Acid Anhydrolase from Alteromonas undina," Applied and Environmental Microbiology, Sep. 1993, vol. 59 No. 9, pp. 3138-3140.
Raveh et al., "Human Butyrylcholinesterase as a General Prophylactic Antidote for Nerve Agent Toxicity," Biochemical Pharmacology, 1993, vol. 45, No. 12, pp. 2465-2474.
Munnecke, "Enzymatic Hydrolysis of Organophosphate Insecticides, a Possible Pesticide Disposal Method," Applied and Environmental Microbiology, Jul. 1976, vol. 32, No. 1, pp. 7-13.
Sethunathan et al., "A *Flavobacterium* sp. that degrades diazinon and parathion," Canadian Journal of Microbiology, 1973, vol. 19, pp. 873-875.
Horne et al., "The phosphotriesterase gene opdA in Agrobacterium radiobacter P230 is transposable," FEMS Microbiology Letters, 2003, pp. 1-8.
Merone et al., "A thermostable phosphotriesterase from the archaeon Sulfolobus solfataricus: cloning, overexpression and properties," Extremophiles, 2005, pp. 297-305.

(Continued)

*Primary Examiner* — Anand U Desai
(74) *Attorney, Agent, or Firm* — Nixon & Vanderhye

(57) ABSTRACT

Disclosed are mutated phosphotriesterase enzymes with improved stability and activity, as well as their use in particular for degrading organophosphorus compounds.

25 Claims, 2 Drawing Sheets

Specification includes a Sequence Listing.

(56) References Cited

OTHER PUBLICATIONS

Jackson et al., "The structure of an enzyme-product complex reveals the critical role of a terminal hydroxide nucleophile in the bacterial phosphotriesterase mechanism," Biochimica et Biophysica Acta, 2005, pp. 56-64.
Jackson et al., "In Crystallo Capture of a Michaelis Complex and Product-binding Modes of a Bacterial Phosphotriesterase," Journal of Molecular Biology, 2008, vol. 375, pp. 1189-1196.
Wong et al., "The Reaction Mechanism of Paraoxon Hydrolysis by Phosphotriesterase from Combined QM/MM Simulations," Biochemistry, 2007, vol. 46, pp. 13352-13369.
Elias et al., "Structural Basis for Natural Lactonase and Promiscuous Phosphotriesterase Activities," Journal of Molecular Biology, 2008, vol. 379, pp. 1017-1028.
Del Vecchio et al., "Structural determinants of the high thermal stability of SsoPox from the hyperthermophilic archaeon Sulfolobus solfataricus," Extremophiles, 2009, pp. 461-470.

* cited by examiner

SEQ ID NO : 13

SEQUENCE LISTING

<160> NUMBER OF SEQ ID NOS: 13

<210> SEQ ID NO 1
<211> LENGTH: 333
<212> TYPE: PRT
<213> ORGANISM: Artificial sq.
<220> FEATURE:
<223> OTHER INFORMATION: Sequence WT

<400> SEQUENCE: 1

Met Gly Asp Arg Ile Asn Thr Val Arg Gly Pro Ile Thr Ile Ser Glu
1 5 10 15

Ala Gly Phe Thr Leu Thr His Glu His Ile Cys Gly Ser Ser Ala Gly
20 25 30

Phe Leu Arg Ala Trp Pro Glu Phe Phe Gly Ser Arg Lys Ala Leu Ala
35 40 45

Glu Lys Ala Val Arg Gly Leu Arg Arg Ala Arg Ala Ala Gly Val Arg
50 55 60

Thr Ile Val Asp Val Ser Thr Phe Asp Ile Gly Arg Asp Val Ser Leu
65 70 75 80

Leu Ala Glu Val Ser Arg Ala Ala Asp Val His Ile Val Ala Ala Thr
85 90 95

Gly Leu Trp Phe Asp Pro Pro Leu Ser Met Arg Leu Arg Ser Val Glu
100 105 110

Glu Leu Thr Gln Phe Phe Leu Arg Glu Ile Gln Tyr Gly Ile Glu Asp
115 120 125

Thr Gly Ile Arg Ala Gly Ile Ile Lys Val Ala Thr Thr Gly Lys Ala

-continued

```
    130                 135                 140

Thr Pro Phe Gln Glu Leu Val Leu Lys Ala Ala Ala Arg Ala Ser Leu
145                 150                 155                 160

Ala Thr Gly Val Pro Val Thr Thr His Thr Ala Ala Ser Gln Arg Asp
                165                 170                 175

Gly Glu Gln Gln Ala Ala Ile Phe Glu Ser Glu Gly Leu Ser Pro Ser
            180                 185                 190

Arg Val Cys Ile Gly His Ser Asp Asp Thr Asp Asp Leu Ser Tyr Leu
        195                 200                 205

Thr Ala Leu Ala Ala Arg Gly Tyr Leu Ile Gly Leu Asp His Ile Pro
    210                 215                 220

His Ser Ala Ile Gly Leu Glu Asp Asn Ala Ser Ala Ser Ala Leu Leu
225                 230                 235                 240

Gly Ile Arg Ser Trp Gln Thr Arg Ala Leu Leu Ile Lys Ala Leu Ile
                245                 250                 255

Asp Gln Gly Tyr Met Lys Gln Ile Leu Val Ser Asn Asp Trp Leu Phe
            260                 265                 270

Gly Phe Ser Ser Tyr Val Thr Asn Ile Met Asp Val Met Asp Arg Val
        275                 280                 285

Asn Pro Asp Gly Met Ala Phe Ile Pro Leu Arg Val Ile Pro Phe Leu
    290                 295                 300

Arg Glu Lys Gly Val Pro Gln Glu Thr Leu Ala Gly Ile Thr Val Thr
305                 310                 315                 320

Asn Pro Ala Arg Phe Leu Ser Pro Thr Leu Arg Ala Ser
                325                 330


<210> SEQ ID NO 2
<211> LENGTH: 333
<212> TYPE: PRT
<213> ORGANISM: Artificial sq.
<220> FEATURE:
<223> OTHER INFORMATION: Siquence WT + 7 mutations ancestrales (T13P;
      I14V ; A60S ; S79R ; Y124H ; I218V ; Q258R)

<400> SEQUENCE: 2

Met Gly Asp Arg Ile Asn Thr Val Arg Gly Pro Ile Pro Val Ser Glu
1               5                   10                  15

Ala Gly Phe Thr Leu Thr His Glu His Ile Cys Gly Ser Ser Ala Gly
            20                  25                  30

Phe Leu Arg Ala Trp Pro Glu Phe Phe Gly Ser Arg Lys Ala Leu Ala
        35                  40                  45

Glu Lys Ala Val Arg Gly Leu Arg Arg Ala Arg Ser Ala Gly Val Arg
    50                  55                  60

Thr Ile Val Asp Val Ser Thr Phe Asp Ile Gly Arg Asp Val Arg Leu
65                  70                  75                  80

Leu Ala Glu Val Ser Arg Ala Ala Asp Val His Ile Val Ala Ala Thr
                85                  90                  95

Gly Leu Trp Phe Asp Pro Pro Leu Ser Met Arg Leu Arg Ser Val Glu
            100                 105                 110

Glu Leu Thr Gln Phe Phe Leu Arg Glu Ile Gln His Gly Ile Glu Asp
        115                 120                 125

Thr Gly Ile Arg Ala Gly Ile Ile Lys Val Ala Thr Thr Gly Lys Ala
    130                 135                 140

Thr Pro Phe Gln Glu Leu Val Leu Lys Ala Ala Ala Arg Ala Ser Leu
145                 150                 155                 160
```

-continued

```
Ala Thr Gly Val Pro Val Thr Thr His Thr Ala Ala Ser Gln Arg Asp
                165                 170                 175

Gly Glu Gln Gln Ala Ala Ile Phe Glu Ser Glu Gly Leu Ser Pro Ser
            180                 185                 190

Arg Val Cys Ile Gly His Ser Asp Asp Thr Asp Asp Leu Ser Tyr Leu
        195                 200                 205

Thr Ala Leu Ala Ala Arg Gly Tyr Leu Val Gly Leu Asp His Ile Pro
    210                 215                 220

His Ser Ala Ile Gly Leu Glu Asp Asn Ala Ser Ala Ser Ala Leu Leu
225                 230                 235                 240

Gly Ile Arg Ser Trp Gln Thr Arg Ala Leu Leu Ile Lys Ala Leu Ile
                245                 250                 255

Asp Arg Gly Tyr Met Lys Gln Ile Leu Val Ser Asn Asp Trp Leu Phe
            260                 265                 270

Gly Phe Ser Ser Tyr Val Thr Asn Ile Met Asp Val Met Asp Arg Val
        275                 280                 285

Asn Pro Asp Gly Met Ala Phe Ile Pro Leu Arg Val Ile Pro Phe Leu
    290                 295                 300

Arg Glu Lys Gly Val Pro Gln Glu Thr Leu Ala Gly Ile Thr Val Thr
305                 310                 315                 320

Asn Pro Ala Arg Phe Leu Ser Pro Thr Leu Arg Ala Ser
                325                 330


<210> SEQ ID NO 3
<211> LENGTH: 333
<212> TYPE: PRT
<213> ORGANISM: Artificial sq.
<220> FEATURE:
<223> OTHER INFORMATION: Siquence WT + 7 mutations ancestrales (T13P;
      I14V ; A60S ; S79R ; Y124H ; I218V ; Q258R) + 2 mutations (H225Y ;
      L271T)

<400> SEQUENCE: 3

Met Gly Asp Arg Ile Asn Thr Val Arg Gly Pro Ile Pro Val Ser Glu
1               5                   10                  15

Ala Gly Phe Thr Leu Thr His Glu His Ile Cys Gly Ser Ser Ala Gly
            20                  25                  30

Phe Leu Arg Ala Trp Pro Glu Phe Phe Gly Ser Arg Lys Ala Leu Ala
        35                  40                  45

Glu Lys Ala Val Arg Gly Leu Arg Arg Ala Arg Ser Ala Gly Val Arg
    50                  55                  60

Thr Ile Val Asp Val Ser Thr Phe Asp Ile Gly Arg Asp Val Arg Leu
65                  70                  75                  80

Leu Ala Glu Val Ser Arg Ala Ala Asp Val His Ile Val Ala Ala Thr
                85                  90                  95

Gly Leu Trp Phe Asp Pro Pro Leu Ser Met Arg Leu Arg Ser Val Glu
            100                 105                 110

Glu Leu Thr Gln Phe Phe Leu Arg Glu Ile Gln His Gly Ile Glu Asp
        115                 120                 125

Thr Gly Ile Arg Ala Gly Ile Ile Lys Val Ala Thr Thr Gly Lys Ala
    130                 135                 140

Thr Pro Phe Gln Glu Leu Val Leu Lys Ala Ala Ala Arg Ala Ser Leu
145                 150                 155                 160

Ala Thr Gly Val Pro Val Thr Thr His Thr Ala Ala Ser Gln Arg Asp
                165                 170                 175

Gly Glu Gln Gln Ala Ala Ile Phe Glu Ser Glu Gly Leu Ser Pro Ser
```

-continued

```
            180                 185                 190

Arg Val Cys Ile Gly His Ser Asp Asp Thr Asp Asp Leu Ser Tyr Leu
        195                 200                 205

Thr Ala Leu Ala Ala Arg Gly Tyr Leu Val Gly Leu Asp His Ile Pro
    210                 215                 220

Tyr Ser Ala Ile Gly Leu Glu Asp Asn Ala Ser Ala Ser Ala Leu Leu
225                 230                 235                 240

Gly Ile Arg Ser Trp Gln Thr Arg Ala Leu Leu Ile Lys Ala Leu Ile
                245                 250                 255

Asp Arg Gly Tyr Met Lys Gln Ile Leu Val Ser Asn Asp Trp Thr Phe
            260                 265                 270

Gly Phe Ser Ser Tyr Val Thr Asn Ile Met Asp Val Met Asp Arg Val
        275                 280                 285

Asn Pro Asp Gly Met Ala Phe Ile Pro Leu Arg Val Ile Pro Phe Leu
    290                 295                 300

Arg Glu Lys Gly Val Pro Gln Glu Thr Leu Ala Gly Ile Thr Val Thr
305                 310                 315                 320

Asn Pro Ala Arg Phe Leu Ser Pro Thr Leu Arg Ala Ser
                325                 330


<210> SEQ ID NO 4
<211> LENGTH: 333
<212> TYPE: PRT
<213> ORGANISM: Artificial sq.
<220> FEATURE:
<223> OTHER INFORMATION: Siquence WT + 7 mutations ancestrales (T13P;
      I14V ; A60S ; S79R ; Y124H ; I218V ; Q258R) + 8 mutations (I74C ;
      F100V ; H222Q ; H225Y ; A238V ; L240M ; I242N ; S276L)

<400> SEQUENCE: 4

Met Gly Asp Arg Ile Asn Thr Val Arg Gly Pro Ile Pro Val Ser Glu
1               5                   10                  15

Ala Gly Phe Thr Leu Thr His Glu His Ile Cys Gly Ser Ser Ala Gly
            20                  25                  30

Phe Leu Arg Ala Trp Pro Glu Phe Phe Gly Ser Arg Lys Ala Leu Ala
        35                  40                  45

Glu Lys Ala Val Arg Gly Leu Arg Arg Ala Arg Ser Ala Gly Val Arg
    50                  55                  60

Thr Ile Val Asp Val Ser Thr Phe Asp Cys Gly Arg Asp Val Arg Leu
65                  70                  75                  80

Leu Ala Glu Val Ser Arg Ala Ala Asp Val His Ile Val Ala Ala Thr
                85                  90                  95

Gly Leu Trp Val Asp Pro Pro Leu Ser Met Arg Leu Arg Ser Val Glu
            100                 105                 110

Glu Leu Thr Gln Phe Phe Leu Arg Glu Ile Gln His Gly Ile Glu Asp
        115                 120                 125

Thr Gly Ile Arg Ala Gly Ile Ile Lys Val Ala Thr Thr Gly Lys Ala
    130                 135                 140

Thr Pro Phe Gln Glu Leu Val Leu Lys Ala Ala Ala Arg Ala Ser Leu
145                 150                 155                 160

Ala Thr Gly Val Pro Val Thr Thr His Thr Ala Ala Ser Gln Arg Asp
                165                 170                 175

Gly Glu Gln Gln Ala Ala Ile Phe Glu Ser Glu Gly Leu Ser Pro Ser
            180                 185                 190

Arg Val Cys Ile Gly His Ser Asp Asp Thr Asp Asp Leu Ser Tyr Leu
        195                 200                 205
```

```
Thr Ala Leu Ala Ala Arg Gly Tyr Leu Val Gly Leu Asp Gln Ile Pro
    210                 215                 220

Tyr Ser Ala Ile Gly Leu Glu Asp Asn Ala Ser Ala Ser Val Leu Met
225                 230                 235                 240

Gly Asn Arg Ser Trp Gln Thr Arg Ala Leu Leu Ile Lys Ala Leu Ile
                245                 250                 255

Asp Arg Gly Tyr Met Lys Gln Ile Leu Val Ser Asn Asp Trp Leu Phe
            260                 265                 270

Gly Phe Ser Leu Tyr Val Thr Asn Ile Met Asp Val Met Asp Arg Val
        275                 280                 285

Asn Pro Asp Gly Met Ala Phe Ile Pro Leu Arg Val Ile Pro Phe Leu
    290                 295                 300

Arg Glu Lys Gly Val Pro Gln Glu Thr Leu Ala Gly Ile Thr Val Thr
305                 310                 315                 320

Asn Pro Ala Arg Phe Leu Ser Pro Thr Leu Arg Ala Ser
                325                 330


<210> SEQ ID NO 5
<211> LENGTH: 333
<212> TYPE: PRT
<213> ORGANISM: Artificial sq.
<220> FEATURE:
<223> OTHER INFORMATION: Siquence WT + 7 mutations ancestrales (T13P;
      I14V ; A60S ; S79R ; Y124H ; I218V ; Q258R) + 9 mutations (K45A ;
      A48V ; F100E ; T141N ; K153R ; H222G ; I242N ; R287S ; P310S)

<400> SEQUENCE: 5

Met Gly Asp Arg Ile Asn Thr Val Arg Gly Pro Ile Pro Val Ser Glu
1               5                   10                  15

Ala Gly Phe Thr Leu Thr His Glu His Ile Cys Gly Ser Ser Ala Gly
            20                  25                  30

Phe Leu Arg Ala Trp Pro Glu Phe Phe Gly Ser Arg Ala Ala Leu Val
        35                  40                  45

Glu Lys Ala Val Arg Gly Leu Arg Arg Ala Arg Ser Ala Gly Val Arg
    50                  55                  60

Thr Ile Val Asp Val Ser Thr Phe Asp Ile Gly Arg Asp Val Arg Leu
65                  70                  75                  80

Leu Ala Glu Val Ser Arg Ala Ala Asp Val His Ile Val Ala Ala Thr
                85                  90                  95

Gly Leu Trp Glu Asp Pro Pro Leu Ser Met Arg Leu Arg Ser Val Glu
            100                 105                 110

Glu Leu Thr Gln Phe Phe Leu Arg Glu Ile Gln His Gly Ile Glu Asp
        115                 120                 125

Thr Gly Ile Arg Ala Gly Ile Ile Lys Val Ala Thr Asn Gly Lys Ala
    130                 135                 140

Thr Pro Phe Gln Glu Leu Val Leu Arg Ala Ala Ala Arg Ala Ser Leu
145                 150                 155                 160

Ala Thr Gly Val Pro Val Thr Thr His Thr Ala Ala Ser Gln Arg Asp
                165                 170                 175

Gly Glu Gln Gln Ala Ala Ile Phe Glu Ser Glu Gly Leu Ser Pro Ser
            180                 185                 190

Arg Val Cys Ile Gly His Ser Asp Asp Thr Asp Asp Leu Ser Tyr Leu
        195                 200                 205

Thr Ala Leu Ala Ala Arg Gly Tyr Leu Val Gly Leu Asp Gly Ile Pro
    210                 215                 220
```

-continued

```
His Ser Ala Ile Gly Leu Glu Asp Asn Ala Ser Ala Ser Ala Leu Leu
225                 230                 235                 240

Gly Asn Arg Ser Trp Gln Thr Arg Ala Leu Leu Ile Lys Ala Leu Ile
                245                 250                 255

Asp Arg Gly Tyr Met Lys Gln Ile Leu Val Ser Asn Asp Trp Leu Phe
            260                 265                 270

Gly Phe Ser Ser Tyr Val Thr Asn Ile Met Asp Val Met Asp Ser Val
        275                 280                 285

Asn Pro Asp Gly Met Ala Phe Ile Pro Leu Arg Val Ile Pro Phe Leu
    290                 295                 300

Arg Glu Lys Gly Val Ser Gln Glu Thr Leu Ala Gly Ile Thr Val Thr
305                 310                 315                 320

Asn Pro Ala Arg Phe Leu Ser Pro Thr Leu Arg Ala Ser
                325                 330


<210> SEQ ID NO 6
<211> LENGTH: 333
<212> TYPE: PRT
<213> ORGANISM: Artificial sq.
<220> FEATURE:
<223> OTHER INFORMATION: Siquence WT + 7 mutations ancestrales (T13P;
      I14V ; A60S ; S79R ; Y124H ; I218V ; Q258R) + 11 mutations (K45A ;
      A48V ; F100E ; T141N ; K153R ; G177D ; D201G ; H222G ; I242N ;
      Y277W ; R287S)

<400> SEQUENCE: 6

Met Gly Asp Arg Ile Asn Thr Val Arg Gly Pro Ile Pro Val Ser Glu
1               5                   10                  15

Ala Gly Phe Thr Leu Thr His Glu His Ile Cys Gly Ser Ser Ala Gly
            20                  25                  30

Phe Leu Arg Ala Trp Pro Glu Phe Phe Gly Ser Arg Ala Ala Leu Val
        35                  40                  45

Glu Lys Ala Val Arg Gly Leu Arg Arg Ala Arg Ser Ala Gly Val Arg
    50                  55                  60

Thr Ile Val Asp Val Ser Thr Phe Asp Ile Gly Arg Asp Val Arg Leu
65                  70                  75                  80

Leu Ala Glu Val Ser Arg Ala Ala Asp Val His Ile Val Ala Ala Thr
                85                  90                  95

Gly Leu Trp Glu Asp Pro Pro Leu Ser Met Arg Leu Arg Ser Val Glu
            100                 105                 110

Glu Leu Thr Gln Phe Phe Leu Arg Glu Ile Gln His Gly Ile Glu Asp
        115                 120                 125

Thr Gly Ile Arg Ala Gly Ile Ile Lys Val Ala Thr Asn Gly Lys Ala
    130                 135                 140

Thr Pro Phe Gln Glu Leu Val Leu Arg Ala Ala Ala Arg Ala Ser Leu
145                 150                 155                 160

Ala Thr Gly Val Pro Val Thr Thr His Thr Ala Ala Ser Gln Arg Asp
                165                 170                 175

Asp Glu Gln Gln Ala Ala Ile Phe Glu Ser Glu Gly Leu Ser Pro Ser
            180                 185                 190

Arg Val Cys Ile Gly His Ser Asp Gly Thr Asp Asp Leu Ser Tyr Leu
        195                 200                 205

Thr Ala Leu Ala Ala Arg Gly Tyr Leu Val Gly Leu Asp Gly Ile Pro
    210                 215                 220

His Ser Ala Ile Gly Leu Glu Asp Asn Ala Ser Ala Ser Ala Leu Leu
225                 230                 235                 240
```

```
Gly Asn Arg Ser Trp Gln Thr Arg Ala Leu Leu Ile Lys Ala Leu Ile
                245                 250                 255

Asp Arg Gly Tyr Met Lys Gln Ile Leu Val Ser Asn Asp Trp Leu Phe
            260                 265                 270

Gly Phe Ser Ser Trp Val Thr Asn Ile Met Asp Val Met Asp Ser Val
        275                 280                 285

Asn Pro Asp Gly Met Ala Phe Ile Pro Leu Arg Val Ile Pro Phe Leu
    290                 295                 300

Arg Glu Lys Gly Val Pro Gln Glu Thr Leu Ala Gly Ile Thr Val Thr
305                 310                 315                 320

Asn Pro Ala Arg Phe Leu Ser Pro Thr Leu Arg Ala Ser
                325                 330


<210> SEQ ID NO 7
<211> LENGTH: 333
<212> TYPE: PRT
<213> ORGANISM: Artificial sq.
<220> FEATURE:
<223> OTHER INFORMATION: Siquence WT + 7 mutations ancestrales (T13P;
      I14V ; A60S ; S79R ; Y124H ; I218V ; Q258R) + 12 mutations (K45A ;
      A48V ; I74A ; F100E ; T141N ; K153R ; G177D ; D201G ; H222G ;
      I242N ; Y277W ; R287S)

<400> SEQUENCE: 7

Met Gly Asp Arg Ile Asn Thr Val Arg Gly Pro Ile Pro Val Ser Glu
1               5                   10                  15

Ala Gly Phe Thr Leu Thr His Glu His Ile Cys Gly Ser Ser Ala Gly
            20                  25                  30

Phe Leu Arg Ala Trp Pro Glu Phe Phe Gly Ser Arg Ala Ala Leu Val
        35                  40                  45

Glu Lys Ala Val Arg Gly Leu Arg Arg Ala Arg Ser Ala Gly Val Arg
    50                  55                  60

Thr Ile Val Asp Val Ser Thr Phe Asp Ala Gly Arg Asp Val Arg Leu
65                  70                  75                  80

Leu Ala Glu Val Ser Arg Ala Ala Asp Val His Ile Val Ala Ala Thr
                85                  90                  95

Gly Leu Trp Glu Asp Pro Pro Leu Ser Met Arg Leu Arg Ser Val Glu
            100                 105                 110

Glu Leu Thr Gln Phe Phe Leu Arg Glu Ile Gln His Gly Ile Glu Asp
        115                 120                 125

Thr Gly Ile Arg Ala Gly Ile Ile Lys Val Ala Thr Asn Gly Lys Ala
    130                 135                 140

Thr Pro Phe Gln Glu Leu Val Leu Arg Ala Ala Ala Arg Ala Ser Leu
145                 150                 155                 160

Ala Thr Gly Val Pro Val Thr Thr His Thr Ala Ala Ser Gln Arg Asp
                165                 170                 175

Asp Glu Gln Gln Ala Ala Ile Phe Glu Ser Glu Gly Leu Ser Pro Ser
            180                 185                 190

Arg Val Cys Ile Gly His Ser Asp Gly Thr Asp Asp Leu Ser Tyr Leu
        195                 200                 205

Thr Ala Leu Ala Ala Arg Gly Tyr Leu Val Gly Leu Asp Gly Ile Pro
    210                 215                 220

His Ser Ala Ile Gly Leu Glu Asp Asn Ala Ser Ala Ser Ala Leu Leu
225                 230                 235                 240

Gly Asn Arg Ser Trp Gln Thr Arg Ala Leu Leu Ile Lys Ala Leu Ile
                245                 250                 255
```

-continued

```
Asp Arg Gly Tyr Met Lys Gln Ile Leu Val Ser Asn Asp Trp Leu Phe
            260                 265                 270

Gly Phe Ser Ser Trp Val Thr Asn Ile Met Asp Val Met Asp Ser Val
        275                 280                 285

Asn Pro Asp Gly Met Ala Phe Ile Pro Leu Arg Val Ile Pro Phe Leu
    290                 295                 300

Arg Glu Lys Gly Val Pro Gln Glu Thr Leu Ala Gly Ile Thr Val Thr
305                 310                 315                 320

Asn Pro Ala Arg Phe Leu Ser Pro Thr Leu Arg Ala Ser
                325                 330


<210> SEQ ID NO 8
<211> LENGTH: 333
<212> TYPE: PRT
<213> ORGANISM: Artificial sq.
<220> FEATURE:
<223> OTHER INFORMATION: Siquence WT + 7 mutations ancestrales (T13P;
      I14V ; A60S ; S79R ; Y124H ; I218V ; Q258R) + 13 mutations (K45A ;
      A48M ; F100E ; T141N ; K153R ; G177D ; D201G ; H222G; A238S ;
      L239W ; I242N ; Y277W ; R287S)

<400> SEQUENCE: 8

Met Gly Asp Arg Ile Asn Thr Val Arg Gly Pro Ile Pro Val Ser Glu
1               5                   10                  15

Ala Gly Phe Thr Leu Thr His Glu His Ile Cys Gly Ser Ser Ala Gly
            20                  25                  30

Phe Leu Arg Ala Trp Pro Glu Phe Phe Gly Ser Arg Ala Ala Leu Met
        35                  40                  45

Glu Lys Ala Val Arg Gly Leu Arg Arg Ala Arg Ser Ala Gly Val Arg
    50                  55                  60

Thr Ile Val Asp Val Ser Thr Phe Asp Ile Gly Arg Asp Val Arg Leu
65                  70                  75                  80

Leu Ala Glu Val Ser Arg Ala Ala Asp Val His Ile Val Ala Ala Thr
                85                  90                  95

Gly Leu Trp Glu Asp Pro Pro Leu Ser Met Arg Leu Arg Ser Val Glu
            100                 105                 110

Glu Leu Thr Gln Phe Phe Leu Arg Glu Ile Gln His Gly Ile Glu Asp
        115                 120                 125

Thr Gly Ile Arg Ala Gly Ile Ile Lys Val Ala Thr Asn Gly Lys Ala
    130                 135                 140

Thr Pro Phe Gln Glu Leu Val Leu Arg Ala Ala Ala Arg Ala Ser Leu
145                 150                 155                 160

Ala Thr Gly Val Pro Val Thr Thr His Thr Ala Ala Ser Gln Arg Asp
                165                 170                 175

Asp Glu Gln Gln Ala Ala Ile Phe Glu Ser Glu Gly Leu Ser Pro Ser
            180                 185                 190

Arg Val Cys Ile Gly His Ser Asp Gly Thr Asp Asp Leu Ser Tyr Leu
        195                 200                 205

Thr Ala Leu Ala Ala Arg Gly Tyr Leu Val Gly Leu Asp Gly Ile Pro
    210                 215                 220

His Ser Ala Ile Gly Leu Glu Asp Asn Ala Ser Ala Ser Ser Trp Leu
225                 230                 235                 240

Gly Asn Arg Ser Trp Gln Thr Arg Ala Leu Leu Ile Lys Ala Leu Ile
                245                 250                 255

Asp Arg Gly Tyr Met Lys Gln Ile Leu Val Ser Asn Asp Trp Leu Phe
            260                 265                 270
```

```
Gly Phe Ser Ser Trp Val Thr Asn Ile Met Asp Val Met Asp Ser Val
        275                 280                 285

Asn Pro Asp Gly Met Ala Phe Ile Pro Leu Arg Val Ile Pro Phe Leu
    290                 295                 300

Arg Glu Lys Gly Val Pro Gln Glu Thr Leu Ala Gly Ile Thr Val Thr
305                 310                 315                 320

Asn Pro Ala Arg Phe Leu Ser Pro Thr Leu Arg Ala Ser
                325                 330


<210> SEQ ID NO 9
<211> LENGTH: 333
<212> TYPE: PRT
<213> ORGANISM: Artificial sq.
<220> FEATURE:
<223> OTHER INFORMATION: Siquence WT + 7 mutations ancestrales (T13P;
      I14V ; A60S ; S79R ; Y124H ; I218V ; Q258R) + 174 mutations
      (K45A ; A48M ; I74A ; F100E ; T141N ; K153R ; G177D ; D201G ;
      H222G ; A238S ; L239W ; I242N ; Y277W ; R287S)

<400> SEQUENCE: 9

Met Gly Asp Arg Ile Asn Thr Val Arg Gly Pro Ile Pro Val Ser Glu
1               5                   10                  15

Ala Gly Phe Thr Leu Thr His Glu His Ile Cys Gly Ser Ser Ala Gly
            20                  25                  30

Phe Leu Arg Ala Trp Pro Glu Phe Phe Gly Ser Arg Ala Ala Leu Met
        35                  40                  45

Glu Lys Ala Val Arg Gly Leu Arg Arg Ala Arg Ser Ala Gly Val Arg
    50                  55                  60

Thr Ile Val Asp Val Ser Thr Phe Asp Ala Gly Arg Asp Val Arg Leu
65                  70                  75                  80

Leu Ala Glu Val Ser Arg Ala Ala Asp Val His Ile Val Ala Ala Thr
                85                  90                  95

Gly Leu Trp Glu Asp Pro Pro Leu Ser Met Arg Leu Arg Ser Val Glu
            100                 105                 110

Glu Leu Thr Gln Phe Phe Leu Arg Glu Ile Gln His Gly Ile Glu Asp
        115                 120                 125

Thr Gly Ile Arg Ala Gly Ile Ile Lys Val Ala Thr Asn Gly Lys Ala
    130                 135                 140

Thr Pro Phe Gln Glu Leu Val Leu Arg Ala Ala Ala Arg Ala Ser Leu
145                 150                 155                 160

Ala Thr Gly Val Pro Val Thr Thr His Thr Ala Ala Ser Gln Arg Asp
                165                 170                 175

Asp Glu Gln Gln Ala Ala Ile Phe Glu Ser Glu Gly Leu Ser Pro Ser
            180                 185                 190

Arg Val Cys Ile Gly His Ser Asp Gly Thr Asp Asp Leu Ser Tyr Leu
        195                 200                 205

Thr Ala Leu Ala Ala Arg Gly Tyr Leu Val Gly Leu Asp Gly Ile Pro
    210                 215                 220

His Ser Ala Ile Gly Leu Glu Asp Asn Ala Ser Ala Ser Ser Trp Leu
225                 230                 235                 240

Gly Asn Arg Ser Trp Gln Thr Arg Ala Leu Leu Ile Lys Ala Leu Ile
                245                 250                 255

Asp Arg Gly Tyr Met Lys Gln Ile Leu Val Ser Asn Asp Trp Leu Phe
            260                 265                 270

Gly Phe Ser Ser Trp Val Thr Asn Ile Met Asp Val Met Asp Ser Val
        275                 280                 285
```

-continued

```
Asn Pro Asp Gly Met Ala Phe Ile Pro Leu Arg Val Ile Pro Phe Leu
    290                 295                 300

Arg Glu Lys Gly Val Pro Gln Glu Thr Leu Ala Gly Ile Thr Val Thr
305                 310                 315                 320

Asn Pro Ala Arg Phe Leu Ser Pro Thr Leu Arg Ala Ser
                325                 330


<210> SEQ ID NO 10
<211> LENGTH: 333
<212> TYPE: PRT
<213> ORGANISM: Artificial sq.
<220> FEATURE:
<223> OTHER INFORMATION: Siquence WT + 7 mutations ancestrales (T13P;
      I14V ; A60S ; S79R ; Y124H ; I218V ; Q258R) + 14 mutations (K45A ;
      A48M ; F100E ; T141N ; K153R ; G177D ; D201G ; H222G ; S235M ;
      A238S ; L239W ; I242N ; Y277W ; R287S)

<400> SEQUENCE: 10

Met Gly Asp Arg Ile Asn Thr Val Arg Gly Pro Ile Pro Val Ser Glu
1               5                   10                  15

Ala Gly Phe Thr Leu Thr His Glu His Ile Cys Gly Ser Ser Ala Gly
            20                  25                  30

Phe Leu Arg Ala Trp Pro Glu Phe Phe Gly Ser Arg Ala Ala Leu Met
        35                  40                  45

Glu Lys Ala Val Arg Gly Leu Arg Arg Ala Arg Ser Ala Gly Val Arg
    50                  55                  60

Thr Ile Val Asp Val Ser Thr Phe Asp Ile Gly Arg Asp Val Arg Leu
65                  70                  75                  80

Leu Ala Glu Val Ser Arg Ala Ala Asp Val His Ile Val Ala Ala Thr
                85                  90                  95

Gly Leu Trp Glu Asp Pro Pro Leu Ser Met Arg Leu Arg Ser Val Glu
            100                 105                 110

Glu Leu Thr Gln Phe Phe Leu Arg Glu Ile Gln His Gly Ile Glu Asp
        115                 120                 125

Thr Gly Ile Arg Ala Gly Ile Ile Lys Val Ala Thr Asn Gly Lys Ala
    130                 135                 140

Thr Pro Phe Gln Glu Leu Val Leu Arg Ala Ala Ala Arg Ala Ser Leu
145                 150                 155                 160

Ala Thr Gly Val Pro Val Thr Thr His Thr Ala Ala Ser Gln Arg Asp
                165                 170                 175

Asp Glu Gln Gln Ala Ala Ile Phe Glu Ser Glu Gly Leu Ser Pro Ser
            180                 185                 190

Arg Val Cys Ile Gly His Ser Asp Gly Thr Asp Asp Leu Ser Tyr Leu
        195                 200                 205

Thr Ala Leu Ala Ala Arg Gly Tyr Leu Val Gly Leu Asp Gly Ile Pro
    210                 215                 220

His Ser Ala Ile Gly Leu Glu Asp Asn Ala Met Ala Ser Ser Trp Leu
225                 230                 235                 240

Gly Asn Arg Ser Trp Gln Thr Arg Ala Leu Leu Ile Lys Ala Leu Ile
                245                 250                 255

Asp Arg Gly Tyr Met Lys Gln Ile Leu Val Ser Asn Asp Trp Leu Phe
            260                 265                 270

Gly Phe Ser Ser Trp Val Thr Asn Ile Met Asp Val Met Asp Ser Val
        275                 280                 285

Asn Pro Asp Gly Met Ala Phe Ile Pro Leu Arg Val Ile Pro Phe Leu
    290                 295                 300
```

Arg Glu Lys Gly Val Pro Gln Glu Thr Leu Ala Gly Ile Thr Val Thr
305 310 315 320

Asn Pro Ala Arg Phe Leu Ser Pro Thr Leu Arg Ala Ser
325 330

<210> SEQ ID NO 11
<211> LENGTH: 333
<212> TYPE: PRT
<213> ORGANISM: Artificial sq.
<220> FEATURE:
<223> OTHER INFORMATION: Siquence WT + 7 mutations ancestrales (T13P; I14V ; A60S ; S79R ; Y124H ; I218V ; Q258R) + 15 mutations (K45A ; A48M ; I74A ; F100E ; T141N ; K153R ; G177D ; D201G ; H222G ; S235M ; A238S ; L239W ; I242N ; Y277W ; R287S)

<400> SEQUENCE: 11

Met Gly Asp Arg Ile Asn Thr Val Arg Gly Pro Ile Pro Val Ser Glu
1 5 10 15

Ala Gly Phe Thr Leu Thr His Glu His Ile Cys Gly Ser Ser Ala Gly
20 25 30

Phe Leu Arg Ala Trp Pro Glu Phe Phe Gly Ser Arg Ala Ala Leu Met
35 40 45

Glu Lys Ala Val Arg Gly Leu Arg Arg Ala Arg Ser Ala Gly Val Arg
50 55 60

Thr Ile Val Asp Val Ser Thr Phe Asp Ala Gly Arg Asp Val Arg Leu
65 70 75 80

Leu Ala Glu Val Ser Arg Ala Ala Asp Val His Ile Val Ala Ala Thr
85 90 95

Gly Leu Trp Glu Asp Pro Pro Leu Ser Met Arg Leu Arg Ser Val Glu
100 105 110

Glu Leu Thr Gln Phe Phe Leu Arg Glu Ile Gln His Gly Ile Glu Asp
115 120 125

Thr Gly Ile Arg Ala Gly Ile Ile Lys Val Ala Thr Asn Gly Lys Ala
130 135 140

Thr Pro Phe Gln Glu Leu Val Leu Arg Ala Ala Ala Arg Ala Ser Leu
145 150 155 160

Ala Thr Gly Val Pro Val Thr Thr His Thr Ala Ala Ser Gln Arg Asp
165 170 175

Asp Glu Gln Gln Ala Ala Ile Phe Glu Ser Glu Gly Leu Ser Pro Ser
180 185 190

Arg Val Cys Ile Gly His Ser Asp Gly Thr Asp Asp Leu Ser Tyr Leu
195 200 205

Thr Ala Leu Ala Ala Arg Gly Tyr Leu Val Gly Leu Asp Gly Ile Pro
210 215 220

His Ser Ala Ile Gly Leu Glu Asp Asn Ala Met Ala Ser Ser Trp Leu
225 230 235 240

Gly Asn Arg Ser Trp Gln Thr Arg Ala Leu Leu Ile Lys Ala Leu Ile
245 250 255

Asp Arg Gly Tyr Met Lys Gln Ile Leu Val Ser Asn Asp Trp Leu Phe
260 265 270

Gly Phe Ser Ser Trp Val Thr Asn Ile Met Asp Val Met Asp Ser Val
275 280 285

Asn Pro Asp Gly Met Ala Phe Ile Pro Leu Arg Val Ile Pro Phe Leu
290 295 300

Arg Glu Lys Gly Val Pro Gln Glu Thr Leu Ala Gly Ile Thr Val Thr
305 310 315 320

```
Asn Pro Ala Arg Phe Leu Ser Pro Thr Leu Arg Ala Ser
                325                 330


<210> SEQ ID NO 12
<211> LENGTH: 333
<212> TYPE: PRT
<213> ORGANISM: Artificial sq.
<220> FEATURE:
<223> OTHER INFORMATION: Siquence WT + 7 mutations ancestrales (T13P;
      I14V ; A60S ; S79R ; Y124H ; I218V ; Q258R) + 15 mutations (K45A ;
      A48M ; I74C ; F100E ; T141N ; K153R ; G177D ; D201G ; H222G ;
      S235M ; A238S ; L239W ; I242N ; Y277W ; R287S)

<400> SEQUENCE: 12

Met Gly Asp Arg Ile Asn Thr Val Arg Gly Pro Ile Pro Val Ser Glu
1               5                   10                  15

Ala Gly Phe Thr Leu Thr His Glu His Ile Cys Gly Ser Ser Ala Gly
            20                  25                  30

Phe Leu Arg Ala Trp Pro Glu Phe Phe Gly Ser Arg Ala Ala Leu Met
        35                  40                  45

Glu Lys Ala Val Arg Gly Leu Arg Arg Ala Arg Ser Ala Gly Val Arg
    50                  55                  60

Thr Ile Val Asp Val Ser Thr Phe Asp Cys Gly Arg Asp Val Arg Leu
65                  70                  75                  80

Leu Ala Glu Val Ser Arg Ala Ala Asp Val His Ile Val Ala Ala Thr
                85                  90                  95

Gly Leu Trp Glu Asp Pro Pro Leu Ser Met Arg Leu Arg Ser Val Glu
            100                 105                 110

Glu Leu Thr Gln Phe Phe Leu Arg Glu Ile Gln His Gly Ile Glu Asp
        115                 120                 125

Thr Gly Ile Arg Ala Gly Ile Ile Lys Val Ala Thr Asn Gly Lys Ala
    130                 135                 140

Thr Pro Phe Gln Glu Leu Val Leu Arg Ala Ala Ala Arg Ala Ser Leu
145                 150                 155                 160

Ala Thr Gly Val Pro Val Thr Thr His Thr Ala Ala Ser Gln Arg Asp
                165                 170                 175

Asp Glu Gln Gln Ala Ala Ile Phe Glu Ser Glu Gly Leu Ser Pro Ser
            180                 185                 190

Arg Val Cys Ile Gly His Ser Asp Gly Thr Asp Asp Leu Ser Tyr Leu
        195                 200                 205

Thr Ala Leu Ala Ala Arg Gly Tyr Leu Val Gly Leu Asp Gly Ile Pro
    210                 215                 220

His Ser Ala Ile Gly Leu Glu Asp Asn Ala Met Ala Ser Ser Trp Leu
225                 230                 235                 240

Gly Asn Arg Ser Trp Gln Thr Arg Ala Leu Leu Ile Lys Ala Leu Ile
                245                 250                 255

Asp Arg Gly Tyr Met Lys Gln Ile Leu Val Ser Asn Asp Trp Leu Phe
            260                 265                 270

Gly Phe Ser Ser Trp Val Thr Asn Ile Met Asp Val Met Asp Ser Val
        275                 280                 285

Asn Pro Asp Gly Met Ala Phe Ile Pro Leu Arg Val Ile Pro Phe Leu
    290                 295                 300

Arg Glu Lys Gly Val Pro Gln Glu Thr Leu Ala Gly Ile Thr Val Thr
305                 310                 315                 320

Asn Pro Ala Arg Phe Leu Ser Pro Thr Leu Arg Ala Ser
                325                 330
```

<210> SEQ ID NO 13
<211> LENGTH: 333
<212> TYPE: PRT
<213> ORGANISM: Artificial sq.
<220> FEATURE:
<223> OTHER INFORMATION: Siquence WT + 8 mutations (I74C ; F100V ; H222Q ; H225Y ; A238V ; L240M ; I242N ; S276L)

<400> SEQUENCE: 13

```
Met Gly Asp Arg Ile Asn Thr Val Arg Gly Pro Ile Thr Ile Ser Glu
1               5                   10                  15

Ala Gly Phe Thr Leu Thr His Glu His Ile Cys Gly Ser Ser Ala Gly
            20                  25                  30

Phe Leu Arg Ala Trp Pro Glu Phe Phe Gly Ser Arg Lys Ala Leu Ala
        35                  40                  45

Glu Lys Ala Val Arg Gly Leu Arg Arg Ala Arg Ala Ala Gly Val Arg
    50                  55                  60

Thr Ile Val Asp Val Ser Thr Phe Asp Cys Gly Arg Asp Val Ser Leu
65                  70                  75                  80

Leu Ala Glu Val Ser Arg Ala Ala Asp Val His Ile Val Ala Ala Thr
                85                  90                  95

Gly Leu Trp Val Asp Pro Pro Leu Ser Met Arg Leu Arg Ser Val Glu
            100                 105                 110

Glu Leu Thr Gln Phe Phe Leu Arg Glu Ile Gln Tyr Gly Ile Glu Asp
        115                 120                 125

Thr Gly Ile Arg Ala Gly Ile Ile Lys Val Ala Thr Thr Gly Lys Ala
    130                 135                 140

Thr Pro Phe Gln Glu Leu Val Leu Lys Ala Ala Ala Arg Ala Ser Leu
145                 150                 155                 160

Ala Thr Gly Val Pro Val Thr Thr His Thr Ala Ala Ser Gln Arg Asp
                165                 170                 175

Gly Glu Gln Gln Ala Ala Ile Phe Glu Ser Glu Gly Leu Ser Pro Ser
            180                 185                 190

Arg Val Cys Ile Gly His Ser Asp Asp Thr Asp Asp Leu Ser Tyr Leu
        195                 200                 205

Thr Ala Leu Ala Ala Arg Gly Tyr Leu Ile Gly Leu Asp Gln Ile Pro
    210                 215                 220

Tyr Ser Ala Ile Gly Leu Glu Asp Asn Ala Ser Ala Ser Val Leu Met
225                 230                 235                 240

Gly Asn Arg Ser Trp Gln Thr Arg Ala Leu Leu Ile Lys Ala Leu Ile
                245                 250                 255

Asp Gln Gly Tyr Met Lys Gln Ile Leu Val Ser Asn Asp Trp Leu Phe
            260                 265                 270

Gly Phe Ser Leu Tyr Val Thr Asn Ile Met Asp Val Met Asp Arg Val
        275                 280                 285

Asn Pro Asp Gly Met Ala Phe Ile Pro Leu Arg Val Ile Pro Phe Leu
    290                 295                 300

Arg Glu Lys Gly Val Pro Gln Glu Thr Leu Ala Gly Ile Thr Val Thr
305                 310                 315                 320

Asn Pro Ala Arg Phe Leu Ser Pro Thr Leu Arg Ala Ser
                325                 330
```

MUTATED PTE ENZYMES

BACKGROUND OF THE INVENTION

Field of the Invention

The present invention concerns mutated phosphotriesterase enzymes having improved stability and activity, as well as their use in particular for degrading organophosphorus compounds.

Description of the Related Art

Organophosphate (OPs) insecticides have become the most widely used insecticides today. OPs are used in agriculture, at home, in gardens and in the veterinary practice.

Since these compounds inhibit some esterase enzymes, exposure to OPs can lead to serious toxicity, in several ways.

Irreversible inhibition of acetylcholinesterase (a key enzyme of the mammalian nervous system) by OPs causes severe damage for all vertebrates. Loss of enzyme function leads to accumulation of acetylcholine in different compartments of the body, causing muscle contraction, paralysis and respiratory depression. Increased pulmonary secretions with respiratory failure are the usual cause of death from organophosphate poisoning.

Some OPs have also been developed during the Second World War: the discovery of OPs with improved toxicity and/or higher stability has led to the development of chemical warfar agents such as sarin, soman, tabun or VX. Moreover, OP insecticides, being easily accessible and not so less toxic as compared to chemical warfar agents OPs, constitute an important risk for the population.

More recently, the current terrorist risk has led the authorities to consider scenarios of chemical attacks using organophosphate substances such as sarin and faced with these growing threats, the development of antidotes has never been more urgent.

OPs are easily absorbed by the body by inhalation, ingestion or skin penetration because of the hydrophobicity of these molecules. The occurrence of poisoning depends on the absorption rate of the compound. Symptoms of acute OP poisoning occur during or after exposure, within minutes or hours, depending on the type of exposure.

Exposure by inhalation results in the fastest appearance of toxic symptoms, followed by the gastrointestinal route and finally, intoxication by skin contact.

Protective suits and masks do not always offer sufficient protection against OPs. In patients poisoned by OPs via skin, clothing or hair, decontamination must be carried out with medical soap or laundry detergents. Treatment of highly contaminated persons results in administering atropine or diazepam, which antagonize the effects of excessive concentrations of acetylcholine on target organs having muscarinic receptors.

Pralidoxime, a acetylcholinesterase reactivator, reduces nicotine effects such as muscarinic effects of OP poisoning when administered less than 48 hours after poisoning.

Although some progress in terms of prophylaxis has been made with the 10 above-mentioned techniques, existing protections and treatments for these types of poisoning remain unsatisfactory.

The first OP-hydrolases have been identified in several bacteria in the early 90's (Cheng et al., 1993, Appl. Environ. Microbiol, 59: 3138-3140, Raveh et al., 1993, Biochem Pharmacol., 45: 2465-2474). These enzymes are able to catalyze the hydrolysis of phosphotriester bonds in OPs. Unfortunately, due to their low stoichiometric binding capacity to OPs, huge quantity of enzymes is needed to cure poisoned individuals. This renders the use of these enzymes disproportionate and expensive.

Other microbial enzymes generally called phosphotriesterases (PTEs) show preference for organophosphorus compounds with P—O or P—S bonds. These enzymes are members of a superfamily, called aminohydrolases, which are enzymes that catalyse the hydrolysis of a broad range of compounds with different chemical properties (phosphoesters, esters, amides, etc.). Their coding genes, opd (organophosphate degradation), were isolated in soil bacteria such as *Pseudomonas diminuta*, also called *Brevundimonas diminuta* (Munnecke et al., 1976, Appl. Environ. Microbiol., 32: 7-13), *Flavobacterium* sp. (Sethunathan et al., 1973, Can J Microbiol, 19: 873-875) and *Agrobacterium radiobacter* (Horne et al., 2003, FEMS Microbiol Lett, 222: 1-8), and genes similar to opd were also identified in Archea (Merone et al, 2005, Extremophiles, 9: 297-305). The catalytic properties of hyperthermophilic PTEs are extensively studied because of their ability to hydrolyze pesticides and several nerve agents (Jackson et al, 2005, Biochem Biophys Acta, 1752: 56-64/Jackson et al., 2008, J Mol Biol, 375: 1189-1196/Wong et al., 2007, Biochemistry, 46: 13352-13369/Elias et al., 2008, J Mol Biol, 379: 1017-1028/Pompea et al., 2009, Extremophiles, 13: 461-470).

The hyperthermophilic PTEs have the advantage of being very stable and inexpensive to produce due to their capacity to resist to organic solvents or detergents at moderate temperatures. Thus, hyperthermophilic PTEs are promising for the development of bioscavengers for neurotoxic agents.

SUMMARY OF THE INVENTION

One of the aims of the present invention is to provide PTE enzymes having improved stability. Another aim of the present invention is to improve, in addition to stability, the enzymatic activity of such a PTE enzyme.

At its most general aspect, this invention concerns a mutated PTE enzyme derived from the parathion hydrolase of sequence SEQ ID NO: 1, said mutated PTE enzyme has at least 90% identity with SEQ ID NO: 1 and comprises at least the following 7 mutations with respect to the sequence SEQ ID NO: 1:

Substitution of threonine T by proline P, in position 13,
Substitution of isoleucine I by valine V, at position 14,
Substitution of alanine A by serine S, in position 60,
Substitution of serine S by arginine R, in position 79,
Substitution of tyrosine Y by histidine H, in position 124,
Substitution of isoleucine I by valine V, at position 218,
Substitution of glutamine Q by arginine R, at position 258.

The inventors unexpectedly found that specific mutations in the sequence of parathion hydrolase of sequence SEQ ID NO:1 allow obtaining of an enzyme that has retained substantially the same catalytic activity as wild-type parathion hydrolase, but with improved stability. The parathion hydrolase of the so-called "wild-type" sequence is the enzyme of sequence SEQ ID NO: 1.

By "at least 90% identity", it means the value ranges of at least 91%, at least 92%, at least 93%, at least 94%, at least 95%, at least 96%, at least 97%, at least 98%, at least 99% and 100% identity.

By "enzyme with improved stability", it means an enzyme whose melting temperature Tm is increased relative to that of the non-mutated parathion hydrolase.

To fix ideas, the increase in stability can result in an increase in the melting temperature of at least 3% and in particular from at least 3% to 20%.

The expression "substantially identical catalytic activity" corresponds to a variation in the Kcat/Km ratio of the mutated enzyme of less than a factor of 10 compared to the Kcat/Km ratio of the non-mutated enzyme.

For example, Kcat/Km ratios of $6.10^5$ $M^{-1}\cdot s^{-1}$ and $3.10^5$ $M^{-1}\cdot s^{-1}$ are considered sufficiently close (factor 2) to consider that enzymes with such Kcat/Km ratios have substantially identical catalytic activity.

By "position", it means the place of an amino acid in the polypeptide sequence, established from the N-terminal end of the enzyme of sequence SEQ ID NO: 1.

All of the 7 mutations mentioned-above, at positions 13, 14, 60, 79, 124, 218 and 258 with respect to the sequence SEQ ID NO: 1 will subsequently be referred to as mutations of group A.

Thus, the expression "mutations of group A" could be replaced by the following list:

"Substitution of threonine T by proline P, in position 13,
Substitution of isoleucine I by valine V, at position 14,
Substitution of alanine A by serine S, in position 60,
Substitution of serine S by arginine R, in position 79,
Substitution of tyrosine Y by histidine H, in position 124,
Substitution of isoleucine I by valine V, at position 218,
Substitution of glutamine Q by arginine R, at position 258."

By "identity percentage" with respect to a given sequence, it means the percentage of amino acids identical to those of a reference sequence and found at the same positions. Such a percentage of identity is established by a bio-informatics alignment such as BlastP.

By "mutation", it means a point mutation, i.e. the presence of an amino acid at a given position that is different from that of a reference sequence, SEQ ID NO:1 being chosen as the reference sequence.

By substitution, it means the replacement of an amino acid in a given sequence by a different amino acid.

In a particular embodiment, the present invention concerns a mutated PTE enzyme of sequence SEQ ID NO: 2, derived from the parathion hydrolase having the sequence SEQ ID NO: 1, which mutated PTE enzyme has at least 90% identity with SEQ ID NO: 1 and comprises at least the following 7 mutations with respect to the sequence SEQ ID NO: 1:

Substitution of threonine T by proline P, in position 13,
Substitution of isoleucine I by valine V, at position 14,
Substitution of alanine A by serine S, in position 60,
Substitution of serine S by arginine R, in position 79,
Substitution of tyrosine Y by histidine H, in position 124,
Substitution of isoleucine I by valine V, at position 218,
Substitution of glutamine Q by arginine R, at position 258, and a mutated enzyme having at least 90% identity to said sequence SEQ ID NO: 2, subject to the presence of said 7 mutations in said sequence of the mutated enzyme.

According to another particular embodiment, the invention concerns a mutated PTE enzyme, comprising mutations of group A as defined above, in which at least 2 additional amino acids chosen from amino acids at the following positions are mutated:

Amino acid in position 45,
Amino acid in position 48,
Amino acid in position 74,
Amino acid in position 100,
Amino acid in position 141,
Amino acid in position 153,
Amino acid in position 177,
Amino acid in position 201,
Amino acid in position 222,
Amino acid in position 225,
Amino acid in position 235,
Amino acid in position 238,
Amino acid in position 239,
Amino acid in position 240,
Amino acid in position 242,
Amino acid in position 271,
Amino acid in position 276,
Amino acid in position 277,
Amino acid in position 287,
Amino acid in position 310, the positions being defined with respect to the sequence SED ID NO: 1.

Such an enzyme can be obtained from the sequence SEQ ID NO: 1 which, in addition to the mutations of group A, comprises 2 additional mutations at the positions defined above. For example, in addition to the 7 mutations of group A mentioned above, 2 mutations can be performed: one in position 141 and the other in position 277.

By "additional mutation" or "additional substitution", it means any mutation or substitution occurring in addition to those of Group A.

According to another particular embodiment, the invention concerns a mutated PTE enzyme, comprising mutations of group A, in which the additional mutations at the positions defined above are chosen from the following list:

In position 45: substitution of lysine K by alanine A,
In position 48: substitution of alanine A by valine V or methionine M,
In position 74: substitution of isoleucine I by cysteine C or alanine A,
In position 100: substitution of phenylalanine F by glutamic acid E or valine V,
In position 141: substitution of threonine T by asparagine N,
In position 153: substitution of lysine K by arginine R,
In position 177: substitution of glycine G by aspartic acid D,
In position 201: substitution of aspartic acid D by glycine G,
In position 222: substitution of histidine H by glycine G or glutamine Q,
In position 225: substitution of histidine H by tyrosine Y,
In position 235: substitution of serine S by methionine M,
In position 238: substitution of alanine A by valine V or serine S,
In position 239: substitution of leucine L by tryptophan W,
In position 240: substitution of leucine L by methionine M,
In position 242: substitution of isoleucine I by asparagine N,
In position 271: substitution of leucine L by threonine T,
In position 276: substitution of serine S by leucine L,
In position 277: substitution of tyrosine Y by tryptophan W,
In position 287: substitution of arginine R by serine S,
In position 310: substitution of the proline P by the serine S.

For example, such a mutated enzyme can be obtained from the enzyme of sequence SEQ ID NO: 1 which, in addition to the 7 mutations of group A, comprises 2 additional mutations, such as for example a substitution of alanine A in position 48 by valine V or methionine M and the substitution of proline P in position 310 by serine S.

Such a mutated enzyme then comprises 9 mutations with respect to the enzyme of sequence SEQ ID NO: 1, at positions 13, 14, 48, 60, 79, 124, 218, 258 and 310.

According to another particular embodiment, the invention concerns a mutated PTE enzyme comprising only mutations of group A, of sequence SEQ ID NO: 2, in which:

The amino acid at position 45 is lysine K,
The amino acid at position 48 is alanine A,
The amino acid at position 74 is isoleucine I,
The amino acid at position 100 is phenylalanine F,
The amino acid at position 141 is threonine T,
The amino acid at position 153 is lysine K,
The amino acid at position 177 is glycine G,
The amino acid in position 201 is aspartic acid D,
The amino acid in position 222 is histidine H,
The amino acid at position 225 is histidine H,
The amino acid in position 235 is serine S,
The amino acid at position 238 is alanine A,
The amino acid at position 239 is leucine L,
The amino acid at position 240 is leucine L,
The amino acid at position 242 is isoleucine I,
The amino acid in position 271 is leucine L,
The amino acid in position 276 is serine S,
The amino acid at position 277 is tyrosine Y,
The amino acid at position 287 is arginine R,
The amino acid in position 310 is proline P.

Thus, the obtained mutated enzyme comprises only the 7 mutations of group A, with respect to the sequence SEQ ID NO: 1, and therefore has the sequence SEQ ID NO: 2.

According to another particular embodiment, the invention concerns a mutated PTE enzyme comprising the mutations of group A and comprising at least 2 additional mutations, at positions 225 and 271.

According to another particular embodiment, the invention concerns a mutated PTE enzyme of sequence SEQ ID NO: 3, comprising the mutations of group A and in which the at least 2 above additional mutations are as follows:

In position 225: substitution of histidine H by tyrosine Y,
In position 271: substitution of leucine L by threonine T.

Thus, the obtained mutated enzyme comprises the 7 mutations of group A and at least the 2 above additional mutations, its sequence being the sequence SEQ ID NO: 3.

According to another particular embodiment, the invention concerns a mutated PTE enzyme comprising mutations of group A and comprising at least 8 additional mutations, at position 74, 100, 222, 225, 238, 240, 242 and 276.

According to another particular embodiment, the invention concerns a mutated PTE enzyme of sequence SEQ ID NO: 4, comprising the mutations of group A and in which the at least 8 above additional mutations are as follows:

In position 74: substitution of isoleucine I by cysteine,
In position 100: substitution of phenylalanine F by valine V,
In position 222: substitution of histidine H by glutamine 0,
In position 225: substitution of histidine H by tyrosine Y,
In position 238: substitution of alanine A by valine V,
In position 240: substitution of leucine L by methionine M,
In position 242: substitution of isoleucine I by asparagine N,
In position 276: substitution of serine S by leucine L.

Thus, the obtained mutated enzyme comprises the 7 mutations of group A and at least the 8 above additional mutations, its sequence being the sequence SEQ ID NO: 4.

According to another particular embodiment, the invention concerns a mutated PTE enzyme comprising the mutations of group A and comprising at least 9 additional mutations, at position 45, 48, 100, 141, 153, 222, 242, 287 and 310.

According to another particular embodiment, the invention concerns a mutated PTE enzyme of sequence SEQ ID NO: 5, comprising the mutations of group A and in which the at least 9 above additional mutations are as follows:

In position 45: substitution of lysine K by alanine A,
In position 48: substitution of alanine A by valine V,
In position 100: substitution of phenylalanine F by glutamic acid E,
In position 141: substitution of threonine T by asparagine N,
In position 153: substitution of lysine K by arginine R,
In position 222: substitution of histidine H by glycine G,
In position 242: substitution of isoleucine I by asparagine N,
In position 287: substitution of arginine R by serine S,
In position 310: substitution of the proline P by the serine S.

Thus, the mutated enzyme obtained comprises the 7 mutations of group A and at least the 9 above additional mutations, its sequence being the sequence SEQ ID NO: 5.

According to another particular embodiment, the invention concerns a mutated PTE enzyme comprising mutations of group A and comprising at least 11 additional mutations, at position 45, 48, 100, 141, 153, 177, 201, 222, 242, 277 and 287.

According to another particular embodiment, the invention concerns a mutated PTE enzyme of sequence SEQ ID NO: 6, comprising the mutations of group A and in which the at least 11 above additional mutations are as follows:

In position 45: substitution of lysine K by alanine A,
In position 48: substitution of alanine A by valine V,
In position 100: substitution of phenylalanine F by glutamic acid E,
In position 141: substitution of threonine T by asparagine N,
In position 153: substitution of lysine K by arginine R,
In position 177: substitution of glycine G by aspartic acid D,
In position 201: substitution of aspartic acid D by glycine G,
In position 222: substitution of histidine H by glycine G,
In position 242: substitution of isoleucine I by asparagine N,
In position 277: substitution of tyrosine Y by tryptophan W,
In position 287: substitution of arginine R by serine S.

Thus, the obtained mutated enzyme comprises the 7 mutations of group A and at least the 11 above additional mutations, its sequence being the sequence SEQ ID NO: 6.

According to another particular embodiment, the invention concerns a mutated PTE enzyme comprising mutations of group A and comprising at least 12 additional mutations, at position 45, 48, 74, 100, 141, 153, 177, 201, 222, 242, 277 and 287.

According to another particular embodiment, the invention concerns a mutated PTE enzyme of sequence SEQ ID NO: 7, comprising the mutations of group A and in which the at least 12 above additional mutations are as follows:

In position 45: substitution of lysine K by alanine A,
In position 48: substitution of alanine A by valine V,
In position 74: substitution of isoleucine I by alanine A, In position 100: substitution of phenylalanine F by glutamic acid E, In position 141: substitution of threonine T by asparagine N, In position 153: substitution of lysine K by arginine R, In position 177: substitution of glycine G by aspartic acid D, In position 201: substitution of aspartic acid D by glycine G, In position 222: substitution of histidine H by glycine G, In position 242: substitution of isoleucine I by asparagine N, In position 277: substitution of tyrosine Y by tryptophan W, In position 287: substitution of arginine R by serine S.

Thus, the obtained mutated enzyme comprises the 7 mutations of group A and at least the 12 above additional mutations, its sequence being the sequence SEQ ID NO: 7.

According to another particular embodiment, the invention concerns a mutated PTE enzyme comprising mutations of group A and comprising at least 13 additional mutations, at position 45, 48, 100, 141, 153, 177, 201, 222, 238, 239, 242, 277 and 287.

According to another particular embodiment, the invention concerns a mutated PTE enzyme of sequence SEQ ID NO: 8, comprising the mutations of group A and in which the at least 13 above additional mutations are as follows:

In position 45: substitution of lysine K by alanine A,

In position 48: substitution of alanine A by methionine M,

In position 100: substitution of phenylalanine F by glutamic acid E,

In position 141: substitution of threonine T by asparagine N,

In position 153: substitution of lysine K by arginine R,

In position 177: substitution of glycine G by aspartic acid D,

In position 201: substitution of aspartic acid D by glycine G,

In position 222: substitution of histidine H by glycine G,

In position 238: substitution of alanine A by serine S,

In position 239: substitution of leucine L by tryptophan W,

In position 242: substitution of isoleucine I by asparagine N,

In position 277: substitution of tyrosine Y by tryptophan W,

In position 287: substitution of arginine R by serine S.

Thus, the obtained mutated enzyme comprises the 7 mutations of group A and at least the 13 above additional mutations, its sequence being the sequence SEQ ID NO: 8.

According to another particular embodiment, the invention concerns a mutated PTE enzyme comprising mutations of group A and comprising at least 14 additional mutations, at position 45, 48, 74, 100, 141, 153, 177, 201, 222, 238, 239, 242, 277 and 287.

According to another particular embodiment, the invention concerns a mutated PTE enzyme of sequence SEQ ID NO: 9, comprising the mutations of group A and in which the at least 14 above additional mutations are as follows:

In position 45: substitution of lysine K by alanine A,

In position 48: substitution of alanine A by methionine M,

In position 74: substitution of isoleucine I by alanine A,

In position 100: substitution of phenylalanine F by glutamic acid E,

In position 141: substitution of threonine T by asparagine N,

In position 153: substitution of lysine K by arginine R,

In position 177: substitution of glycine G by aspartic acid D,

In position 201: substitution of aspartic acid D by glycine G,

In position 222: substitution of histidine H by glycine G,

In position 238: substitution of alanine A by serine S,

In position 239: substitution of leucine L by tryptophan W,

In position 242: substitution of isoleucine I by asparagine N,

In position 277: substitution of tyrosine Y by tryptophan W,

In position 287: substitution of arginine R by serine S.

Thus, the obtained mutated enzyme comprises the 7 mutations of group A and at least the 14 above additional mutations, its sequence being the sequence SEQ ID NO: 9.

According to another particular embodiment, the invention concerns a mutated PTE enzyme comprising mutations of group A and comprising at least 14 additional mutations, at position 45, 48, 100, 141, 153, 177, 201, 222, 235, 238, 239, 242, 277 and 287.

According to another particular embodiment, the invention concerns a mutated PTE enzyme of sequence SEQ ID NO: 10, comprising the mutations of group A and in which the at least 14 above additional mutations are as follows:

In position 45: substitution of lysine K by alanine A,

In position 48: substitution of alanine A by methionine M,

In position 100: substitution of phenylalanine F by glutamic acid E,

In position 141: substitution of threonine T by asparagine N,

In position 153: substitution of lysine K by arginine R,

In position 177: substitution of glycine G by aspartic acid D,

In position 201: substitution of aspartic acid D by glycine G,

In position 222: substitution of histidine H by glycine G,

In position 235: substitution of serine S by methionine M,

In position 238: substitution of ala nine A by serine S,

In position 239: substitution of leucine L by tryptophan W,

In position 242: substitution of isoleucine I by asparagine N,

In position 277: substitution of tyrosine Y by tryptophan W,

In position 287: substitution of arginine R by serine S.

Thus, the obtained mutated enzyme comprises the 7 mutations of group A and at least the 14 above additional mutations, its sequence being the sequence SEQ ID NO: 10.

According to another particular embodiment, the invention concerns a mutated PTE enzyme comprising mutations of group A and comprising at least 15 additional mutations, at position 45, 48, 74, 100, 141, 153, 177, 201, 222, 235, 238, 239, 242, 277 and 287.

According to another particular embodiment, the invention concerns a mutated PTE enzyme of sequence SEQ ID NO: 11, comprising mutations of group A and in which the at least 15 above additional mutations are as follows:

In position 45: substitution of lysine K by alanine A,

In position 48: substitution of alanine A by methionine M,

In position 74: substitution of isoleucine I by alanine A,

In position 100: substitution of phenylalanine F by glutamic acid E,

In position 141: substitution of threonine T by asparagine N,

In position 153: substitution of lysine K by arginine R,

In position 177: substitution of glycine G by aspartic acid D,

In position 201: substitution of aspartic acid D by glycine G,

In position 222: substitution of histidine H by glycine G,

In position 235: substitution of serine S by methionine M,

In position 238: substitution of alanine A by serine S,

In position 239: substitution of leucine L by tryptophan W,

In position 242: substitution of isoleucine I by asparagine N,

In position 277: substitution of tyrosine Y by tryptophan W,

In position 287: substitution of arginine R by serine S.

Thus, the obtained mutated enzyme comprises the 7 mutations of group A and at least the 15 above additional mutations, its sequence being the sequence SEQ ID NO: 11.

According to another particular embodiment, the invention concerns a mutated PTE enzyme of sequence SEQ ID NO: 12, comprising the mutations of group A and in which the at least 15 above additional mutations are as follows:

In position 45: substitution of lysine K by alanine A,

In position 48: substitution of alanine A by methionine M,

In position 74: substitution of isoleucine I by cysteine C,

In position 100: substitution of phenylalanine F by glutamic acid E,

In position 141: substitution of threonine T by asparagine N,

In position 153: substitution of lysine K by arginine R,

In position 177: substitution of glycine G by aspartic acid D,

In position 201: substitution of aspartic acid D by glycine G,

In position 222: substitution of histidine H by glycine G,

In position 235: substitution of serine S by methionine M,

In position 238: substitution of alanine A by serine S,

In position 239: substitution of leucine L by tryptophan W,

In position 242: substitution of isoleucine I by asparagine N,

In position 277: substitution of tyrosine Y by tryptophan W,

In position 287: substitution of arginine R by serine S.

Thus, the obtained mutated enzyme comprises the 7 mutations of group A and at least the 15 above additional mutations, its sequence being the sequence SEQ ID NO: 12.

According to another particular embodiment, the invention concerns a mutated PTE enzyme according to mutations of group A, of sequence SEQ ID NO: 2, in which:

The amino acid at position 45 is different from alanine A,

The amino acid at position 48 is different from valine V and methionine M,

The amino acid at position 74 is different from cysteine C and alanine A,

The amino acid in position 100 is different from glutamic acid E and valine V,

The amino acid in position 141 is different from asparagine N,

The amino acid in position 153 is different from arginine R,

The amino acid in position 177 is different from aspartic acid D,

The amino acid in position 201 is different from glycine G,

The amino acid in position 222 is different from glycine G and glutamine Q,

The amino acid in position 225 is different from tyrosine Y,

The amino acid in position 235 is different from methionine M,

The amino acid in position 238 is different from valine V and serine S,

The amino acid in position 239 is different from tryptophan W,

The amino acid in position 240 is different from methionine M,

The amino acid in position 242 is different from asparagine N,

The amino acid in position 271 is different from threonine T,

The amino acid in position 276 is different from leucine L,

The amino acid in position 277 is different from tryptophan W,

The amino acid in position 287 is different from serine S,

The amino acid in position 310 is different from serine S.

According to a particularly preferred embodiment, the invention concerns a PTE enzyme of sequences SEQ ID NO: 3, SEQ ID NO: 4 or SEQ ID NO: 5.

One aspect of the present invention concerns the use of at least 7 mutations, in particular 7 mutations, to increase the stability of a phosphotriesterase enzyme (PTE) of sequence SEQ ID NO: 1 capable of hydrolyzing organophosphorus compounds, by substituting in sequence SEQ ID NO: 1:

the amino acid in position 13 by the proline P, the amino acid at position 14 by valine V, the amino acid in position 60 by the serine S, the amino acid at position 79 by arginine R, the amino acid at position 124 by histidine H, the amino acid at position 218 by valine V, the amino acid at position 258 by arginine R, in order to obtain a mutated PTE enzyme, in particular of sequence SEQ ID NO: 2, which has an improved stability compared to the stability of the enzyme of sequence SED ID NO: 1.

As seen above, the 7 mutations at positions 13, 14, 60, 79, 124, 218, 258 constitute the A mutations of group A.

According to another particular embodiment, the invention concerns the use of at least the 7 mutations of group A, combined with additional mutations to increase the stability and the phosphotriesterase (PTE) catalytic activity of the enzyme of sequence SEQ ID NO: 1 capable of hydrolyzing organophosphorus compounds, by performing in sequence SEQ ID NO: 1 at least two additional substitutions chosen from the substitutions of:

the amino acid at position 45 by alanine A, the amino acid at position 48 by valine V or methionine M, the amino acid at position 74 by cysteine C or ala nine A, the amino acid at position 100 by glutamic acid E or valine V, the amino acid in position 141 by asparagine N, the amino acid at position 153 by arginine R, the amino acid at position 177 by aspartic acid D, the amino acid in position 201 by glycine G, the amino acid at position 222 by glycine G or glutamine Q, the amino acid in position 225 by tyrosine Y, the amino acid at position 235 by methionine M, the amino acid at position 238 by valine V or serine 5, the amino acid at position 239 by tryptophan W, the amino acid at position 240 by methionine M, the amino acid in position 242 by asparagine N, the amino acid in position 271 by the threonine T, the amino acid at position 276 by leucine L, the amino acid at position 277 by tryptophan W, the amino acid in position 287 by the serine S, the amino acid in position 310 by the serine S.

to obtain a mutated PTE enzyme that has an improved stability and an improved hydrolysis catalytic activity of organophosphorus compounds, compared to the stability and the catalytic activity of the enzyme of sequence SED ID NO: 1.

By "increased catalytic activity" or "improved catalytic activity", it means an increase of more than a factor of 10 in the Kcat/Km ratio of the mutated enzyme compared to that of wild-type parathion hydrolase, of sequence SEQ ID NO: 1.

For example, a mutated enzyme having a Kcat/Km=$6.10^6$ $M^{-1}\cdot s^{-1}$ will be considered to have an improved catalytic activity compared to an enzyme having a Kcat/Km=$5.10^5$ $M^{-1}\cdot s^{-1}$.

According to another particular embodiment, the PTE enzyme is mutated by the use of at least the 7 mutations of group A, combined with additional mutations to increase the phosphotriesterase (PTE) catalytic activity of the enzyme of sequence SEQ ID NO: 1 capable of hydrolyzing organophosphorus compounds, by performing in sequence SEQ ID NO: 1 at least 2 additional substitutions in order to obtain a mutated enzyme of sequence chosen from the following: SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 or SEQ ID NO: 12.

In a particularly preferred embodiment, the PTE enzyme is mutated by the use of at least the 7 mutations of group A, combined with additional mutations to increase the phosphotriesterase (PTE) catalytic activity of the enzyme of sequence SEQ ID NO: 1 capable of hydrolyzing organophosphorus compounds, by performing in sequence SEQ ID NO: 1 at least 2 additional substitutions to obtain a mutated enzyme of sequence chosen from the following: SEQ ID NO: 3, SEQ ID NO: 4, SEQ ID NO: 5.

Thus, the resulting mutated PTE enzyme has an improved stability and an improved hydrolysis catalytic activity of organophosphorus compounds, compared to the stability and the catalytic activity of the enzyme of sequence SED ID NO: 1.

A particular embodiment concerns the use of at least the 7 mutations of group A, in combination with 8 additional mutations to increase the stability and the phosphotriesterase (PTE) catalytic activity of the enzyme of sequence SEQ ID NO: 1 capable of hydrolyzing organophosphorus compounds, said 8 additional mutations consisting in the substitution in the sequence SEQ ID NO: 1 of:

the amino acid at position 74 by cysteine C, the amino acid at position 100 by valine V, the amino acid at position 222 by glutamine Q, the amino acid in position 225 by tyrosine Y, the amino acid at position 238 by valine V, the amino acid at position 240 by methionine M, the amino acid in position 242 by asparagine N, the amino acid at position 276 by leucine L, to obtain a mutated PTE enzyme of sequence SEQ ID NO: 4 which has an improved stability and an improved hydrolysis catalytic activity of organophosphorus compounds compared to the stability and the catalytic activity of the enzyme of sequence SED ID NO: 1.

In one aspect of the invention, and without limitation, the OP compounds hydrolyzed by the mutated PTE enzymes of the present invention may be organophosphorus insecticides and organophosphates of chemical warfar agents.

In a particular aspect of the present invention, organophosphorus insecticides hydrolyzed by the PTE enzymes of the present invention may be one of the following:

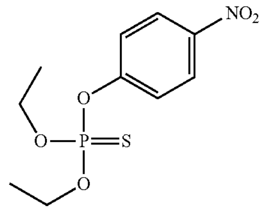

Ethylparathion

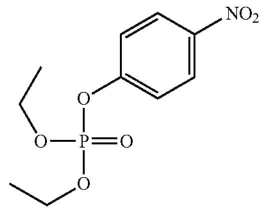

Ethylparaoxon

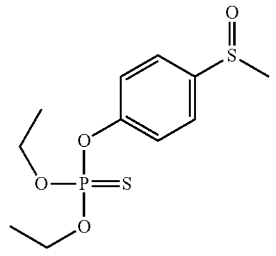

Fensulfothion

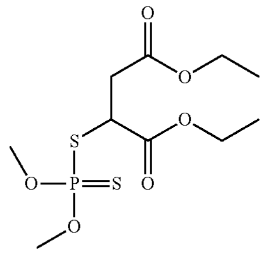

Malathion

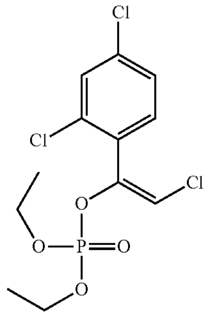

Chlorfenvinphos

-continued

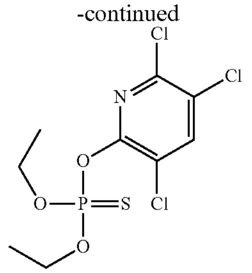

Chlorpyrifos

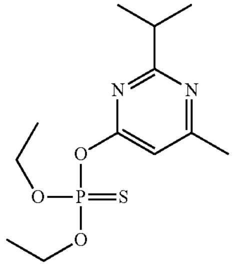

Diazinon

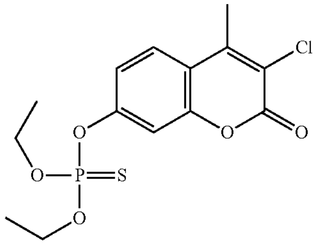

Coumaphos

In a particular aspect of the present invention, the organophosphates of chemical warfar agents hydrolyzed by the PTE enzymes of the present invention may be one of the following:

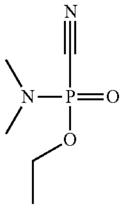

Tabun

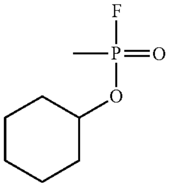

Cyclosarin

-continued

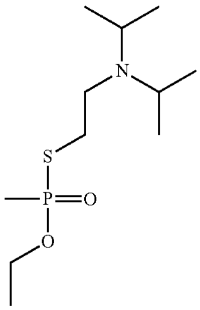

VX

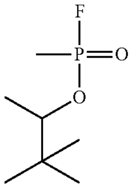

Soman

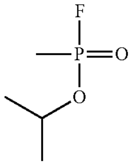

Sarin

In a particularly preferred aspect, the invention concerns the mutated PTE enzyme of sequence SEQ ID NO: 3, said mutated PTE enzyme of sequence SEQ ID NO: 3 being capable of hydrolyzing the following organophosphorus insecticides:

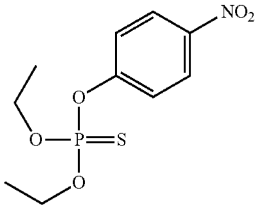

Ethylparathion

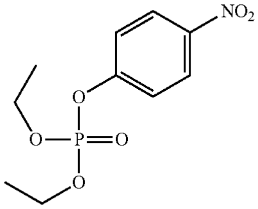

Ethylparaoxon

-continued

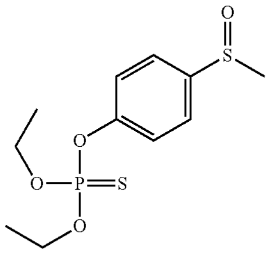

Fensulfothion

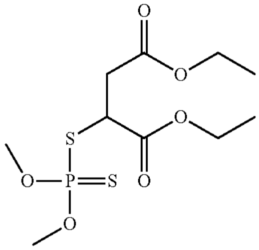

Malathion

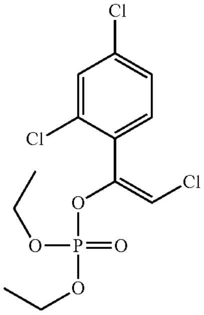

Chlorfenvinphos

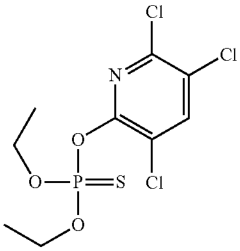

Chlorpyrifos

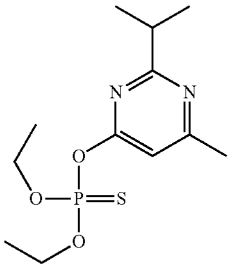

Diazinon

-continued

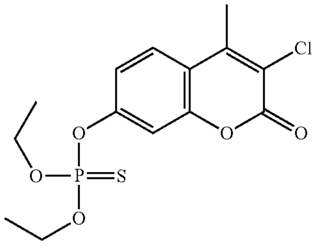

Coumaphos

In a particularly preferred aspect, the invention concerns the mutated PTE enzyme of sequence SEQ ID NO: 3, said mutated PTE enzyme of sequence SEQ ID NO: 3 being capable of hydrolyzing the following organophosphates of chemical warfar agents:

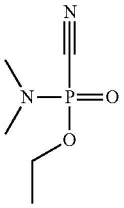

Tabun

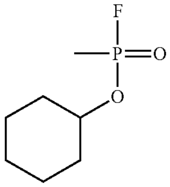

Cyclosarin

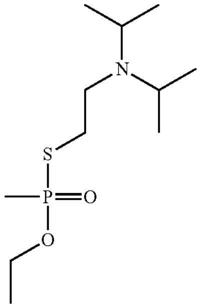

VX

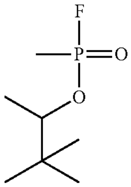

Soman

-continued

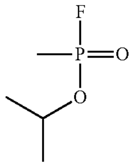

Sarin

In a particularly preferred aspect, the invention concerns the mutated PTE enzyme of sequence SEQ ID NO: 4, said mutated PTE enzyme of sequence SEQ ID NO: 4 being capable of hydrolyzing the following organophosphorus insecticides:

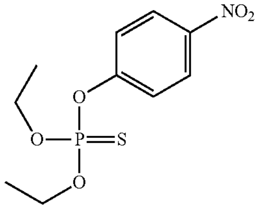

Ethylparathion

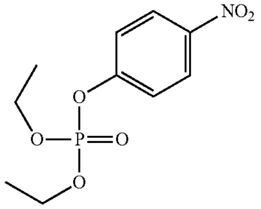

Ethylparaoxon

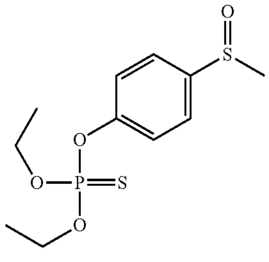

Fensulfothion

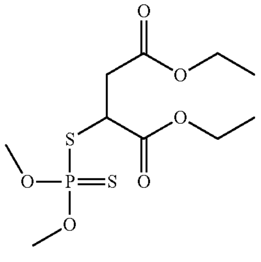

Malathion

-continued

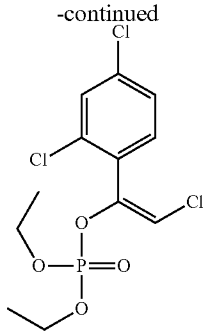

Chlorfenvinphos

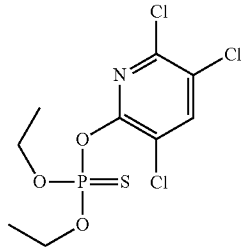

Chlorpyrifos

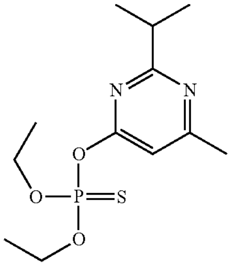

Diazinon

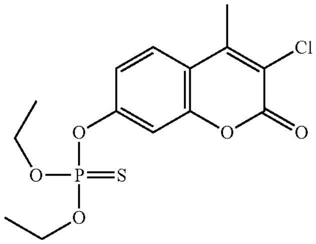

Coumaphos

In a particularly preferred aspect, the invention concerns the mutated PTE enzyme of sequence SEQ ID NO: 4, said mutated PTE enzyme of sequence SEQ ID NO: 4 being capable of hydrolyzing the following organophosphates of chemical warfar agents:

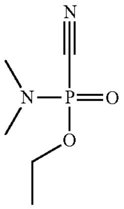

Tabun

-continued

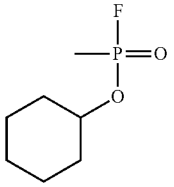

Cyclosarin

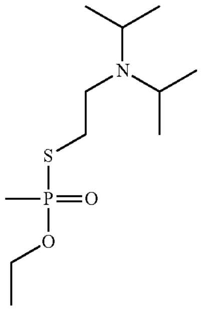

VX

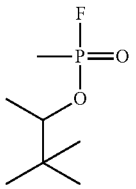

Soman

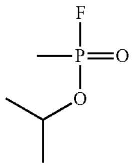

Sarin

In a particularly preferred aspect, the invention concerns the mutated PTE enzyme of sequence SEQ ID NO: 5, said mutated PTE enzyme of sequence SEQ ID NO: 5 being capable of hydrolyzing the following organophosphorus insecticides:

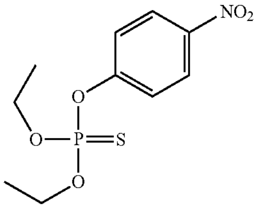

Ethylparathion

-continued

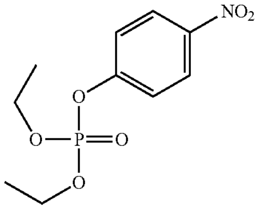

Ethylparaoxon

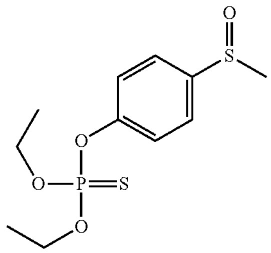

Fensulfothion

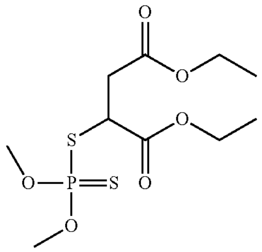

Malathion

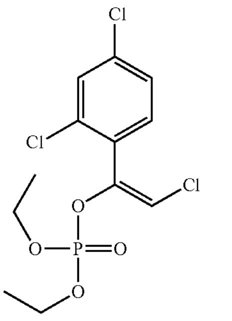

Chlorfenvinphos

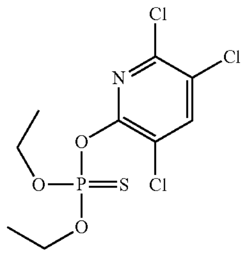

Chlorpyrifos

-continued

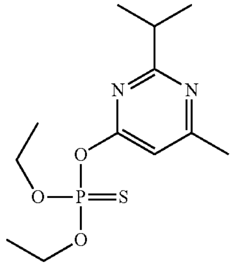

Diazinon

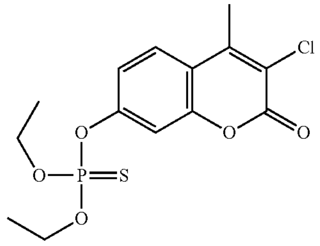

Coumaphos

In a particularly preferred aspect, the invention concerns the mutated PTE enzyme of sequence SEQ ID NO: 5, said mutated PTE enzyme of sequence SEQ ID NO: 5 being capable of hydrolyzing the following organophosphates of chemical warfar agents:

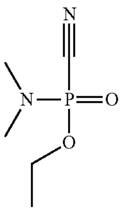

Tabun

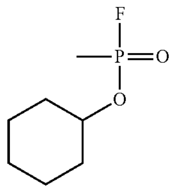

Cyclosarin

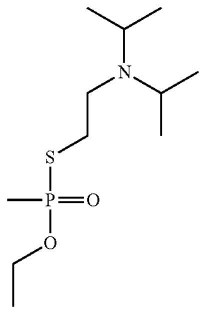

VX

-continued

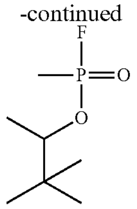

Soman

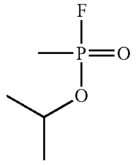

Sarin

Another aspect of the present invention concerns the use of at least one mutated PTE enzyme as defined above, having a phosphotriesterase (PTE) catalytic activity capable of hydrolyzing organophosphorus compounds:

for the decontamination of soils polluted with organophosphorus compounds, or for the decontamination of a surface, skin, mucous membranes or hair contaminated with organophosphorus compounds, or for the prevention or treatment of an internal or of an external poisoning by ingestion or inhalation of an organophosphorus compound, or for the control of pollution of water polluted with organophosphorus compounds, or for the destruction of stocks of neurotoxic agents, or for the decontamination of textiles and filters, or for the decontamination of paints, said at least one mutated PTE enzyme being preferentially chosen from the mutated enzymes of sequence SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 or SEQ ID NO: 12, alone or in combination.

A particularly preferred embodiment of the present invention concerns the use of at least one mutated PTE enzyme of sequence SEQ ID NO: 3, SEQ ID NO: 4 or SEQ ID NO: 5, having a phosphotriesterase (PTE) catalytic activity capable of hydrolyzing organophosphorus compounds:

for the decontamination of soils polluted with organophosphorus compounds, or for the decontamination of a surface, skin, mucous membranes or hair contaminated with organophosphorus compounds, or for the prevention or treatment of an internal or of an external poisoning by ingestion or inhalation of an organophosphorus compound, or for the control of pollution of water polluted with organophosphorus compounds, or for the destruction of stocks of neurotoxic agents, or for the decontamination of textiles and filters, or for the decontamination of paints, Another aspect of the present invention concerns a kit for the decontamination of surfaces, skin or mucous membranes, hair, paints, fabrics or filters contaminated with organophosphorus compounds, said kit comprising at least one mutated PTE enzyme as defined above, having a catalysis activity of organophosphorus compounds and said at least one mutated enzyme being preferably chosen from the mutated enzymes of sequence SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 or SEQ ID NO: 12, alone or in combination with each other.

A particularly preferred embodiment of the present invention concerns a kit for the decontamination of surfaces, skin or mucous membranes, hair, paints, fabrics or filters contaminated with organophosphorus compounds, said kit comprising at least one mutated PTE enzyme of sequence SEQ ID NO: 3, SEQ ID NO: 4 or SEQ ID NO: 5 having a catalysis activity of organophosphorus compounds, alone or in combinations with each other.

Another aspect of the present invention concerns a phytosanitary composition comprising as active ingredient at least one mutated PTE enzyme as defined above, having a catalysis activity of organophosphorus compounds, said at least one mutated enzyme being preferably chosen from mutated enzymes of sequence SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 or SEQ ID NO: 12, alone or in combination with each other.

A particularly preferred embodiment of the present invention concerns a phytosanitary composition comprising as active ingredient at least one mutated PTE enzyme of sequence SEQ ID NO: 3, SEQ ID NO: 4 or SEQ ID NO: 5, having a catalysis activity of organophosphorus compounds, alone or in combinations with each other.

Another aspect of the present invention concerns a pharmaceutical composition comprising as active ingredient at least one mutated PTE enzyme as defined above, having a catalysis activity of organophosphorus compounds, said at least one mutated enzyme being preferably chosen from mutated enzymes of sequence SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 or SEQ ID NO: 12, alone or in combination with each other; in combination with a pharmaceutically acceptable excipient.

A particularly preferred embodiment of the present invention concerns a pharmaceutical composition comprising as active ingredient at least one mutated PTE enzyme of sequence SEQ ID NO: 3, SEQ ID NO: 4 or SEQ ID NO: 5, having a catalysis activity of organophosphorus compounds, alone or in combinations with each other; in combination with a pharmaceutically acceptable excipient.

Another aspect of the present invention concerns a mutated PTE enzyme as defined above, having a catalysis activity of organophosphorus compounds, said at least one mutated enzyme being preferably chosen from mutated enzymes of sequence SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 or SEQ ID NO: 12, alone or in combination with each other, for its use in the treatment or prevention of poisonings by contact, inhalation or ingestion of organophosphate compounds.

A particularly preferred embodiment of the present invention concerns a mutated PTE enzyme of sequence SEQ ID NO: 3, SEQ ID NO: 4 or SEQ ID NO: 5, having a catalysis activity of organophosphorus compounds, alone or in combination with each other, for its use in the treatment or prevention of poisonings by contact, inhalation or ingestion of organophosphorus compounds.

Another aspect of the present invention concerns a method for treating poisonings by contact, inhalation or ingestion of organophosphorus compounds comprising the administration of at least one mutated PTE enzyme as defined above, having a catalysis activity of organophosphorus compounds, said at least one mutated enzyme being preferably chosen from mutated enzymes of sequence SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 or SEQ ID NO: 12, alone or in combination with each other A particularly preferred embodiment of the present invention concerns a method for treating poisonings by contact, inhalation or ingestion of organophosphorus compounds comprising the administration of at least one mutated PTE enzyme of sequence SEQ ID NO: 3, SEQ ID NO: 4 or SEQ ID NO: 5, having a catalysis activity of organophosphate compounds, alone or in combination with each other.

Another aspect of the present invention concerns a method of preventing poisonings by contact, inhalation or ingestion of organophosphorus compounds comprising the administration of at least one mutated PTE enzyme as defined above, having a catalysis activity of organophosphorus compounds, said at least one mutated enzyme being preferably chosen from mutated enzymes of sequence SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 or SEQ ID NO: 12, alone or in combination with each other.

A particularly preferred embodiment of the present invention concerns a method of preventing poisonings by contact, inhalation or ingestion of organophosphorus compounds comprising the administration of at least one mutated PTE enzyme of sequence SEQ ID NO: 3, SEQ ID NO: 4 or SEQ ID NO: 5, having a catalysis activity of organophosphate compounds, alone or in combination with each other

DESCRIPTION OF THE PREFERRED EMBODIMENTS

Materials & Methods

1. Enzyme Production

Figure 1:
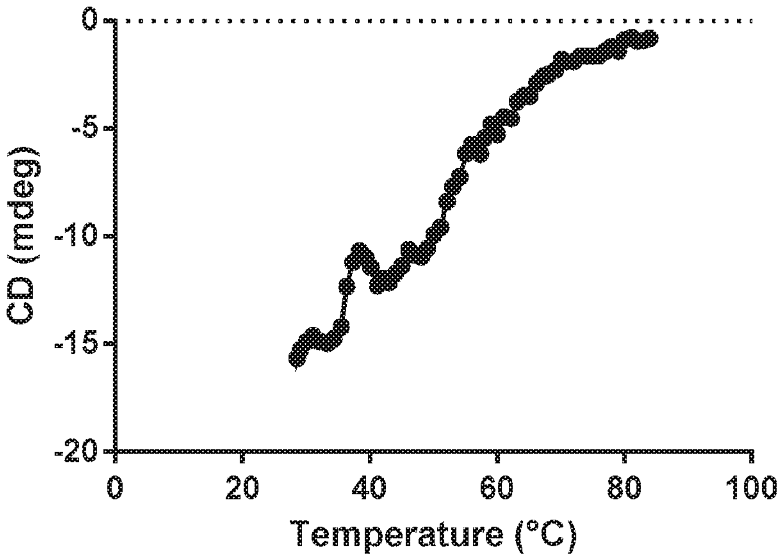
FIG. 1 shows the evolution of circular dichroism (CD) as a function of temperature for the enzyme of sequence SEQ ID NO: 13.

The genes encoding each enzyme were optimized for expression within *E. Coli* and synthesized by GeneScript and then inserted into plasmid pET22b using the restriction enzymes Ndel and Notl.

The production of the protein was carried out within *E. Coli* BL21 (DE3)-pGro7/GroEL in 2 litres of ZYP medium (Tryptone 10 g/L, Yeast extract 5 g/L, $(NH4)_2So_4$ 66 g/L, $KH_2PO_4$ 136 g/L, $Na_2HPO_4$ 142 g/L, Glycerol 250 g (w/v), Glucose 25 g, α-lactose 100 g, 100 μg/ml ampicillin and 344 g/ml chloramphenicol) inoculated overnight in pre-culture with a ratio 1/100.

Growth occurs at 37° C. until a $DO_{600}$ nm=0.8 is reached. Induction is performed by adding L-arabinose 0.2% to the ZYP medium for each PTE as well as $CoCl_2$ 0.2 mM for PTEs of sequence SEQ ID NO: 3 and SEQ ID NO: 4 and $ZnCl_2$ 0.1 mM for PTE of sequence SEQ ID NO: 5 and a temperature change of 16° C. for 20 hours.

The cells are then collected by centrifugation (6420 g, 30 min, CC), then resuspended in the lysis buffer (Tris 50 mM pH 8, NaCl 300 mM, DNAseI 10 μg/mL, lysozyme 0.25 mg/mL, PMSF 0.1 mM) for 4 hours at room temperature and finally stored at −80° C. at night.

The cells undergo sonication (3 steps of 30 seconds) for mechanical lysis (Amplitude 45, time 00:30, pulse on 00:01, pulse off 00:01). Cellular debris are finally removed by centrifugation (11000 rpm, 20 min, CC). Before proceeding to the purification stage, a filtration at 0.8 μm is required.

Purification is done by Strep-Tag affinity chromatography (StrepTrap™ HP 5 ml). Washing and column balancing is carried out with the PTE buffer (50 mM Tris, 300 mM NaCl pH 8) while the sample is eluted with the 50 mM Tris, 300 mM NaCl, 2.5 mM desthiobiotin, pH 8 buffer at a flow rate of 2ml/min.

3. Stability Measurement

Determination of the Melting Temperature

Figure 2:
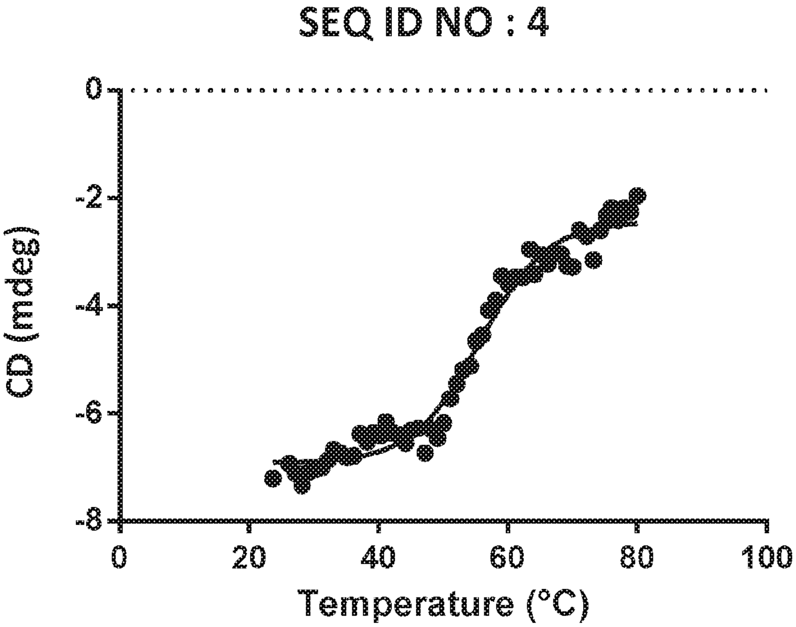
FIG. 2 shows the evolution of circular dichroism (CD) as a function of temperature for the enzyme of sequence SEQ ID NO: 4.

The circular dichroism spectrum was obtained by using a Jasco J-815 CD spectrometer with a Pelletier type temperature control system (Jasco MPTC-4905) in a 1 mm thick Starna® quartz cell and using the Spectra Manager software. The experiments were performed in 50 mM Tris buffer at pH 8. Since protein concentrations were in the range of 0.1-0.2 mg/mL, denaturation was performed at 222 nm with a temperature increase of 25 to 85° C. (at 5° C./min). The data were analyzed with GraphPad Prism 6, using Boltzmann's sigmoid equation. The results are visible in FIGS. 1 and 2 and in Table 1 which compares the melting temperature for the enzyme of sequence SEQ ID NO: 4 with that of the enzyme of sequence SEQ ID NO: 13 (influence of the presence of ancestral mutations on the stability of the enzyme).

TABLE 1

Melting temperature (Tm) as a function of the presence or absence of ancestral mutations. The presence of ancestral mutations (SEQ ID NO: 4) causes an increase in the melting temperature of the enzyme, and therefore its stability with respect to the enzyme without said ancestral mutations (SEQ ID NO: 13)

| PTE | Tm (° C.) |
|---|---|
| SEQ ID NO: 13 | 52.01 |
| SEQ ID NO: 4 | 55.64 |

4. Activity Measurement

Determination of the Activity on Ethyl-Paraoxon of Formula:

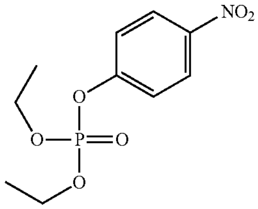 [SMILES: CCOP(=O)(OCC)Oc1ccc([N+](=O)[O-])cc1]

The data were analyzed with Graph Pad Prism 6, using "one phase decay" type modeling. The results are expressed in Table 2 which compares the values of the Kcat/Km ratios for enzymes of sequence SEQ ID NO: 4 and SEQ ID NO: 13 with respect to ethyl paroxon (influence of the presence of ancestral mutations on the catalytic activity of the enzyme with respect to this substrate).

PTE Buffer: Sorting 50 mM, NaCl 300 mM, $CoCl_2$100 μM, pH 8.

TABLE 2

Catalytic activity towards the ethyl-paraoxon of the enzyme of sequence SEQ ID NO: 13 and SEQ ID NO: 4.

| PTE | kcat/kM (M-1 · s-1) |
|---|---|
| SEQ ID NO: 13 | $6 \cdot 10^5$ |
| SEQ ID NO: 4 | $3 \cdot 10^5$ |

Determination of the Activity on DEVX of Formula:

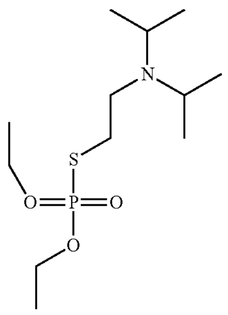

The data were analyzed with GraphPad Prism 6, using a modeling according to the Michaelis-Menten equation. The results are expressed in Table 3 which compares the values of Kcat, Km and Kcat/Km ratios for enzymes of sequence SEQ ID NO: 4 and SEQ ID NO: 13 with respect to DEVX (influence of the presence of ancestral mutations on the catalytic activity of the enzyme with respect to this substrate).

Buffer: NaCl 300 mM, TRIS 50 mM, $CoCl_2$ 100 μM, DTNB 4 mM, pH8.

TABLE 3

Catalytic activity towards the DEVX of the enzyme of sequence SEQ ID NO: 13 and SEQ ID NO: 4.

| PTE | kcat (s-1) | kM (M) | kcat/kM (M-1 · s-1) |
|---|---|---|---|
| SEQ ID NO: 13 | 3.356 | 0.001767 | $\approx 1.9 \cdot 10^3$ |
| SEQ ID NO: 4 | $3 \cdot 10^5$ | 0.001317 | $\approx 1.3 \cdot 10^3$ |

5. Measurement of the Activity of the Mutated ETPs of the Invention on Organophosphate insecticides The catalytic parameters of the mutated PTEs of the invention, in particular mutated PTEs of sequences SEQ ID NO: 3, SEQ ID NO: 4 or SEQ ID NO: 5, are measured at 25° C. in triplicate in 96-well plates with a reaction volume of 200 μL and recorded by a microplate reader (Synergy HT, BioTek, USA) in a 6.2 mm cell using the Gen5.1 software.

Kinetic assays are performed at organophosphorus insecticide concentrations between 0.05 and 2 mM. The hydrolysis efficiency of organophosphorus insecticides by the mutated PTEs of the invention is determined by measuring absorbance or fluorescence for 10 min using a microplate reader. The catalytic efficiency kcat/KM is then determined. Kinetic assays performed in buffer activity (HEPES 50 mM or Tris pH 8.0, NaCl 150 mM). Catalytic parameters are obtained by adjusting the data to the Michaelis-Menten (MM) equation.

The organophosphorus insecticides used to measure the activity of the mutated ETPs of the invention are as follows:

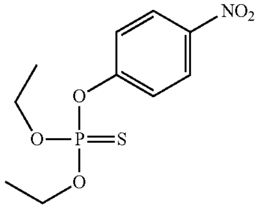

Ethylparathion

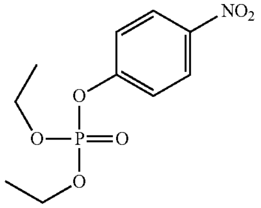

Ethylparaoxon

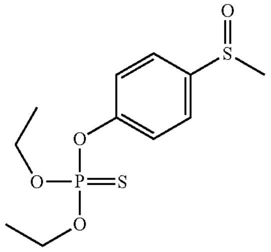

Fensulfothion

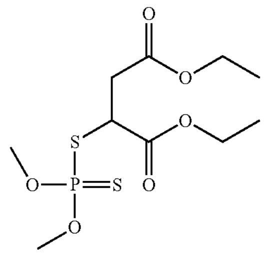

Malathion

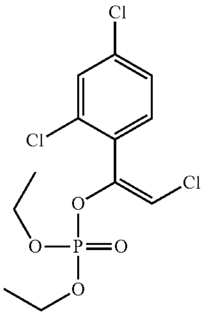

Chlorfenvinphos

-continued

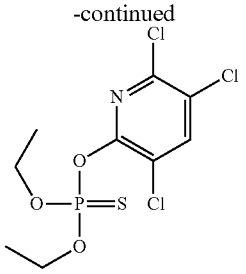

Chlorpyrifos

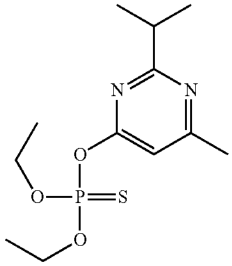

Diazinon

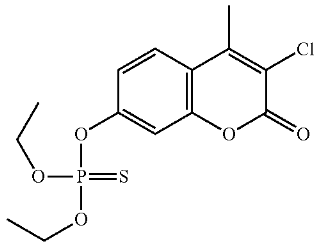

Coumaphos

6. Measurement of the Activity of the Mutated PTEs of the Invention on Organophosphorus of Chemical Warfar Agents a) Degradation Kinetics and NMR Analysis:

The degradation of organophosphorus of chemical warfar agents (CWNA), in particular Soman and VX, by the mutated PTE enzymes of the invention, in particular mutated PTEs of sequences SEQ ID NO: 3, SEQ ID NO: 4 or SEQ ID NO: 5, is monitored over time by NMR 31P.

Up to 10 μl of CWNA are placed in an NMR tube and 0.6 to 1.0 mL of the mutated PTE enzyme of the invention, including mutated PTEs of sequences SEQ ID NO: 3, SEQ ID NO: 4 or SEQ ID NO: 5, or water (control) are added. The signal is recorded at room temperature (about 23° C.) and the signals are measured every 10 minutes for 1 hour.

The effectiveness of CWNA degradation is determined by measuring the integral of the product as the fraction of the sum of all the 31P integrals. The obtained values are reported as the standard deviation of the mean of two separate degradation measurements.

b) Surface Decontamination:

The effectiveness of the decontamination of surfaces contaminated with CWNA, in particular Soman and VX, by the mutated PTEs of the invention, in particular mutated PTEs of sequences SEQ ID NO: 3, SEQ ID NO: 4 or SEQ ID NO: 5, is evaluated over time The material panels (5×5 cm) are impregnated with CWNA to achieve a contamination of 10 g/m2. Then, the panels are immersed in a solution containing the PTEs of the invention, in particular mutated PTEs of sequences SEQ ID NO: 3, SEQ ID NO: 4 or SEQ ID NO: 5, for a duration ranging from 15 minutes to 1 hour.

The panels are then washed with water and carefully dried with a wipe without rubbing. Any residual CWNA agent on the panel is then extracted with a suitable solvent and analysed and quantified by gas chromatography coupled with mass spectrometry (GC-MS).

The organophosphorus of chemical warfar agents used to measure the activity of the mutated PTEs of the invention and their ability to decontaminate impregnated surfaces are as follows:

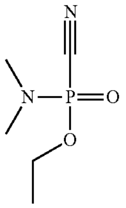

Tabun

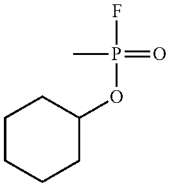

Cyclosarin

-continued

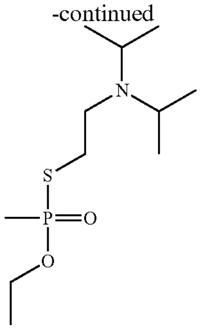

VX

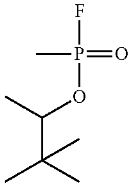

Soman

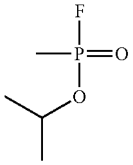

Sarin

The invention claimed is:

1. Mutated phosphotriesterase (PTE) enzyme of sequence SEQ ID NO: 2, derived from parathion hydrolase having sequence SEQ ID NO: 1, wherein said mutated PTE enzyme has at least 95% identity with SEQ ID NO: 1 and contains at least the following 7 mutations with respect to sequence SEQ ID NO: 1:

Substitution of threonine T by proline P, in position 13,
Substitution of isoleucine I by valine V, at position 14,
Substitution of alanine A by serine S, in position 60,
Substitution of serine S by arginine R, in position 79,
Substitution of tyrosine Y by histidine H, in position 124,
Substitution of isoleucine I by valine V, at position 218,
Substitution of glutamine Q by arginine R, at position 258, and a mutated enzyme having at least 95% identity to said sequence SEQ ID NO: 2, subject to the presence of said 7 mutations in said sequence of the mutated enzyme.

2. The mutated PTE enzyme according to claim 1, wherein at least 2 amino acids chosen from amino acids at the following positions are mutated:

Amino acid in position 45,
Amino acid in position 48,
Amino acid in position 74,
Amino acid in position 100,
Amino acid in position 141,
Amino acid in position 153,
Amino acid in position 177,
Amino acid in position 201,
Amino acid in position 222,
Amino acid in position 225,
Amino acid in position 235,
Amino acid in position 238,
Amino acid in position 239,
Amino acid in position 240,
Amino acid in position 242,
Amino acid in position 271,
Amino acid in position 276,
Amino acid in position 277,
Amino acid in position 287,
Amino acid in position 310, positions being defined with respect to the sequence SED ID NO: 1, in particular in which the mutations at the said positions are chosen from the following list:

In position 45: substitution of lysine K by alanine A,
In position 48: substitution of alanine A by valine V or methionine M,
In position 74: substitution of isoleucine I by cysteine C or alanine A,
In position 100: substitution of phenylalanine F by glutamic acid E or valine V,
In position 141: substitution of threonine T by asparagine N,
In position 153: substitution of lysine K by arginine R,
In position 177: substitution of glycine G by aspartic acid D,
In position 201: substitution of aspartic acid D by glycine G,
In position 222: substitution of histidine H by glycine G or glutamine Q,
In position 225: substitution of histidine H by tyrosine Y,
In position 235: substitution of serine S by methionine M,
In position 238: substitution of alanine A by valine V or serine S,
In position 239: substitution of leucine L by tryptophan W,
In position 240: substitution of leucine L by methionine M,
In position 242: substitution of isoleucine I by asparagine N,
In position 271: substitution of leucine L by threonine T,
In position 276: substitution of serine S by leucine L,
In position 277: substitution of tyrosine Y by tryptophan W,
In position 287: substitution of arginine R by serine S,
In position 310: substitution of the proline P by the serine S.

3. The mutated PTE enzyme according to claim 1, having at least 2 mutations, in position 225 and 271.

4. The mutated PTE enzyme according to claim 1, having at least 2 mutations, in position 225 and 271, said mutated PTE enzyme being of sequence SED ID NO: 3, wherein the at least 2 mutations are as follows:

In position 225: substitution of histidine H by tyrosine Y,
In position 271: substitution of leucine L by threonine T.

5. The mutated PTE enzyme according to claim 1, having at least 8 mutations, at position 74, 100, 222, 225, 238, 240, 242 and 276, in particular of sequence ID NO: 4 in which the at least 8 mutations are as follows:

In position 74: substitution of isoleucine I by cysteine,
In position 100: substitution of phenylalanine F by valine V,
In position 222: substitution of histidine H by glutamine Q,
In position 225: substitution of histidine H by tyrosine Y,
In position 238: substitution of alanine A by valine V,
In position 240: substitution of leucine L by methionine M,
In position 242: substitution of isoleucine I by asparagine N,
In position 276: substitution of serine S by leucine L.

6. The mutated PTE enzyme according to claim 1, having at least 9 mutations, in position 45, 48, 100, 141, 153, 222, 242, 287 and 310, in particular of sequence ID NO: 5 in which the at least 9 mutations are as follows:

In position 45: substitution of lysine K by alanine A,
In position 48: substitution of alanine A by valine V,
In position 100: substitution of phenylalanine F by glutamic acid E,
In position 141: substitution of threonine T by asparagine N,
In position 153: substitution of lysine K by arginine R,
In position 222: substitution of histidine H by glycine G,
In position 242: substitution of isoleucine I by asparagine N,
In position 287: substitution of arginine R by serine S,
In position 310: substitution of the proline P by the serine S.

7. The mutated PTE enzyme according to claim 1, having at least 11 mutations, in position 45, 48, 100, 141, 153, 177, 201, 222, 242, 277 and 287, in particular of sequence SED ID NO: 6, in which the at least 11 mutations are as follows:

In position 45: substitution of lysine K by alanine A,
In position 48: substitution of alanine A by valine V,
In position 100: substitution of phenylalanine F by glutamic acid E,
In position 141: substitution of threonine T by asparagine N,
In position 153: substitution of lysine K by arginine R,
In position 177: substitution of glycine G by aspartic acid D,
In position 201: substitution of aspartic acid D by glycine G, In position 222: substitution of histidine H by glycine G,
In position 242: substitution of isoleucine I by asparagine N,
In position 277: substitution of tyrosine Y by tryptophan W,
In position 287: substitution of arginine R by serine S.

8. The mutated PTE enzyme according to claim 1, having at least 12 mutations, in position 45, 48, 74, 100, 141, 153, 177, 201, 222, 242, 277 and 287 in particular of sequence SED ID NO: 7, in which the at least 12 mutations are as follows:

In position 45: substitution of lysine K by alanine A,
In position 48: substitution of alanine A by valine V,
In position 74: substitution of isoleucine I by alanine A,
In position 100: substitution of phenylalanine F by glutamic acid E,
In position 141: substitution of threonine T by asparagine N,
In position 153: substitution of lysine K by arginine R,
In position 177: substitution of glycine G by aspartic acid D,
In position 201: substitution of aspartic acid D by glycine G,
In position 222: substitution of histidine H by glycine G,
In position 242: substitution of isoleucine I by asparagine N,
In position 277: substitution of tyrosine Y by tryptophan W,
In position 287: substitution of arginine R by serine S.

9. The mutated PTE enzyme according to claim 1, having at least 13 mutations, in position 45, 48, 100, 141, 153, 177, 201, 222, 238, 239, 242, 277 and 287 in particular of sequence SED ID NO: 8, in which the at least 13 mutations are as follows:

In position 45: substitution of lysine K by alanine A,
In position 48: substitution of alanine A by methionine M,
In position 100: substitution of phenylalanine F by glutamic acid E,
In position 141: substitution of threonine T by asparagine N,
In position 153: substitution of lysine K by arginine R,
In position 177: substitution of glycine G by aspartic acid D,
In position 201: substitution of aspartic acid D by glycine G,
In position 222: substitution of histidine H by glycine G,
In position 238: substitution of alanine A by serine S,
In position 239: substitution of leucine L by tryptophan W,
In position 242: substitution of isoleucine I by asparagine N,
In position 277: substitution of tyrosine Y by tryptophan W,
In position 287: substitution of arginine R by serine S.

10. The mutated PTE enzyme according to claim 1, having at least 14 mutations, in position 45, 48, 74, 100, 141, 153, 177, 201, 222, 238, 239, 242, 277 and 287 in particular of sequence SED ID NO: 9, wherein the at least 14 mutations are as follows:

In position 45: substitution of lysine K by alanine A,
In position 48: substitution of alanine A by methionine M,
In position 74: substitution of isoleucine I by alanine A,
In position 100: substitution of phenylalanine F by glutamic acid E,
In position 141: substitution of threonine T by asparagine N,
In position 153: substitution of lysine K by arginine R,
In position 177: substitution of glycine G by aspartic acid D,
In position 201: substitution of aspartic acid D by glycine G,
In position 222: substitution of histidine H by glycine G,
In position 238: substitution of alanine A by serine S,
In position 239: substitution of leucine L by tryptophan W,
In position 242: substitution of isoleucine I by asparagine N,
In position 277: substitution of tyrosine Y by tryptophan W,
In position 287: substitution of arginine R by serine S.

11. The mutated PTE enzyme according to claim 1, having at least 14 mutations, in position 45, 48, 100, 141, 153, 177, 201, 222, 235, 238, 239, 242, 277 and 287 in particular of sequence SED ID NO: 10, in which the at least 14 mutations are as follows:

In position 45: substitution of lysine K by alanine A,
In position 48: substitution of alanine A by methionine M,
In position 100: substitution of phenylalanine F by glutamic acid E,
In position 141: substitution of threonine T by asparagine N,
In position 153: substitution of lysine K by arginine R,
In position 177: substitution of glycine G by aspartic acid D,
In position 201: substitution of aspartic acid D by glycine G,
In position 222: substitution of histidine H by glycine G,
In position 235: substitution of serine S by methionine M,
In position 238: substitution of alanine A by serine S,
In position 239: substitution of leucine L by tryptophan W,
In position 242: substitution of isoleucine I by asparagine N,
In position 277: substitution of tyrosine Y by tryptophan W,
In position 287: substitution of arginine R by serine S.

12. The mutated PTE enzyme according to claim 1, having at least 15 mutations, in position 45, 48, 74, 100, 141, 153, 177, 201, 222, 235, 238, 239, 242, 277 and 287 in particular of sequence SED ID NO: 11, in which the at least 15 mutations are the as follows:

In position 45: substitution of lysine K by alanine A,
In position 48: substitution of alanine A by methionine M,
In position 74: substitution of isoleucine I by alanine A,
In position 100: substitution of phenylalanine F by glutamic acid E,
In position 141: substitution of threonine T by asparagine N,
In position 153: substitution of lysine K by arginine R,
In position 177: substitution of glycine G by aspartic acid D,
In position 201: substitution of aspartic acid D by glycine G,
In position 222: substitution of histidine H by glycine G,
In position 235: substitution of serine S by methionine M,
In position 238: substitution of alanine A by serine S,
In position 239: substitution of leucine L by tryptophan W,
In position 242: substitution of isoleucine I by asparagine N,
In position 277: substitution of tyrosine Y by tryptophan W, In position 287: substitution of arginine R by serine S, or in particular of sequence SED ID NO: 12, in which the at least 15 mutations are as follows:

In position 45: substitution of lysine K by alanine A,

In position 48: substitution of alanine A by methionine M,

In position 74: substitution of isoleucine I by cysteine C,

In position 100: substitution of phenylalanine F by glutamic acid E,

In position 141: substitution of threonine T by asparagine N,

In position 153: substitution of lysine K by arginine R,

In position 177: substitution of glycine G by aspartic acid D,

In position 201: substitution of aspartic acid D by glycine G,

In position 222: substitution of histidine H by glycine G,

In position 235: substitution of serine S by methionine M,

In position 238: substitution of alanine A by serine S,

In position 239: substitution of leucine L by tryptophan W,

In position 242: substitution of isoleucine I by asparagine N,

In position 277: substitution of tyrosine Y by tryptophan W,

In position 287: substitution of arginine R by serine S.

13. The mutated PTE enzyme of sequence SEQ ID NO: 2 according to claim 1, wherein:

The amino acid at position 45 is different from alanine A,

The amino acid at position 48 is different from valine V and methionine M,

The amino acid at position 74 is different from cysteine C and alanine A,

The amino acid in position 100 is different from glutamic acid E and valine V,

The amino acid in position 141 is different from asparagine N,

The amino acid in position 153 is different from arginine R,

The amino acid in position 177 is different from aspartic acid D,

The amino acid in position 201 is different from glycine G,

The amino acid in position 222 is different from glycine G and glutamine Q,

The amino acid in position 225 is different from tyrosine Y,

The amino acid in position 235 is different from methionine M,

The amino acid in position 238 is different from valine V and serine S,

The amino acid in position 239 is different from tryptophan W,

The amino acid in position 240 is different from methionine M,

The amino acid in position 242 is different from asparagine N,

The amino acid in position 271 is different from threonine T,

The amino acid in position 276 is different from leucine L,

The amino acid in position 277 is different from tryptophan W,

The amino acid in position 287 is different from serine S,

The amino acid in position 310 is different from serine S.

14. Composition comprising as active ingredient at least one mutated PTE enzyme according to claim 1, and having a catalysis activity of organophosphorus compounds.

15. A method of preventing or treating poisonings by contact, inhalation or ingestion of organophosphorus compounds comprising administering, in a subject in need thereof, a mutated PTE enzymes according to claim 1, having catalysis activity of organophosphorus compounds.

16. The composition according to claim 14, said at least one mutated enzyme is chosen from mutated enzymes of sequence SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 or SEQ ID NO: 12, alone or in combination with each other.

17. The method of preventing or treating poisonings according to claim 15, said at least one mutated enzyme is chosen from mutated enzymes of sequence SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 or SEQ ID NO: 12, alone or in combination with each other.

18. Mutated phosphotriesterase (PTE) enzyme of sequence SEQ ID NO: 2, derived from parathion hydrolase having sequence SEQ ID NO: 1, wherein said mutated PTE enzyme has at least 90% identity with SEQ ID NO: 1 and contains at least the following 7 mutations with respect to sequence SEQ ID NO: 1:

Substitution of threonine T by proline P, in position 13,

Substitution of isoleucine I by valine V, at position 14,

Substitution of alanine A by serine S, in position 60,

Substitution of serine S by arginine R, in position 79,

Substitution of tyrosine Y by histidine H, in position 124,

Substitution of isoleucine I by valine V, at position 218,

Substitution of glutamine Q by arginine R, at position 258, and a mutated enzyme having at least 90% identity to said sequence SEQ ID NO: 2, subject to the presence of said 7 mutations in said sequence of the mutated enzyme; and wherein at least 2 amino acids chosen from amino acids at the following positions are mutated:

Amino acid in position 45,

Amino acid in position 48,

Amino acid in position 74,

Amino acid in position 100,

Amino acid in position 141,

Amino acid in position 153,

Amino acid in position 177,

Amino acid in position 201,

Amino acid in position 222,

Amino acid in position 225,

Amino acid in position 235,

Amino acid in position 238,

Amino acid in position 239,

Amino acid in position 240,

Amino acid in position 242,

Amino acid in position 271,

Amino acid in position 276,

Amino acid in position 277,

Amino acid in position 287,

Amino acid in position 310, positions being defined with respect to the sequence SED ID NO: 1, in particular in which the mutations at the said positions are chosen from the following list:

In position 45: substitution of lysine K by alanine A,

In position 48: substitution of alanine A by valine V or methionine M,

In position 74: substitution of isoleucine I by cysteine C or alanine A,

In position 100: substitution of phenylalanine F by glutamic acid E or valine V,
In position 141: substitution of threonine T by asparagine N,
In position 153: substitution of lysine K by arginine R,
In position 177: substitution of glycine G by aspartic acid D,
In position 201: substitution of aspartic acid D by glycine G,
In position 222: substitution of histidine H by glycine G or glutamine Q,
In position 225: substitution of histidine H by tyrosine Y,
In position 235: substitution of serine S by methionine M,
In position 238: substitution of alanine A by valine V or serine S,
In position 239: substitution of leucine L by tryptophan W,
In position 240: substitution of leucine L by methionine M,
In position 242: substitution of isoleucine I by asparagine N,
In position 271: substitution of leucine L by threonine T,
In position 276: substitution of serine S by leucine L,
In position 277: substitution of tyrosine Y by tryptophan W,
In position 287: substitution of arginine R by serine S,
In position 310: substitution of the proline P by the serine S.

19. The mutated PTE enzyme according to claim 18, having at least 2 mutations, in position 225 and 271.

20. The mutated PTE enzyme according to claim 18, having at least 8 mutations, at position 74, 100, 222, 225, 238, 240, 242 and 276, in particular of sequence ID NO: 4 in which the at least 8 mutations are as follows:
In position 74: substitution of isoleucine I by cysteine,
In position 100: substitution of phenylalanine F by valine V,
In position 222: substitution of histidine H by glutamine Q,
In position 225: substitution of histidine H by tyrosine Y,
In position 238: substitution of alanine A by valine V,
In position 240: substitution of leucine L by methionine M,
In position 242: substitution of isoleucine I by asparagine N,
In position 276: substitution of serine S by leucine L.

21. The mutated PTE enzyme according to claim 18, having at least 9 mutations, in position 45, 48, 100, 141, 153, 222, 242, 287 and 310, in particular of sequence ID NO: 5 in which the at least 9 mutations are as follows:
In position 45: substitution of lysine K by alanine A,
In position 48: substitution of alanine A by valine V,
In position 100: substitution of phenylalanine F by glutamic acid E,
In position 141: substitution of threonine T by asparagine N,
In position 153: substitution of lysine K by arginine R,
In position 222: substitution of histidine H by glycine G,
In position 242: substitution of isoleucine I by asparagine N,
In position 287: substitution of arginine R by serine S,
In position 310: substitution of the proline P by serine S.

22. The mutated PTE enzyme according to claim 18, having at least 11 mutations, in position 45, 48, 100, 141, 153, 177, 201, 222, 242, 277 and 287, in particular of sequence SED ID NO: 6, in which the at least 11 mutations are as follows:
In position 45: substitution of lysine K by alanine A,
In position 48: substitution of alanine A by valine V,
In position 100: substitution of phenylalanine F by glutamic acid E,
In position 141: substitution of threonine T by asparagine N,
In position 153: substitution of lysine K by arginine R,
In position 177: substitution of glycine G by aspartic acid D,
In position 201: substitution of aspartic acid D by glycine G,
In position 222: substitution of histidine H by glycine G,
In position 242: substitution of isoleucine I by asparagine N,
In position 277: substitution of tyrosine Y by tryptophan W,
In position 287: substitution of arginine R by serine S.

23. The mutated PTE enzyme according to claim 18, having at least 12 mutations, in position 45, 48, 74, 100, 141, 153, 177, 201, 222, 242, 277 and 287 in particular of sequence SED ID NO: 7, in which the at least 12 mutations are as follows:
In position 45: substitution of lysine K by alanine A,
In position 48: substitution of alanine A by valine V,
In position 74: substitution of isoleucine I by alanine A,
In position 100: substitution of phenylalanine F by glutamic acid E,
In position 141: substitution of threonine T by asparagine N,
In position 153: substitution of lysine K by arginine R,
In position 177: substitution of glycine G by aspartic acid D,
In position 201: substitution of aspartic acid D by glycine G,
In position 222: substitution of histidine H by glycine G,
In position 242: substitution of isoleucine I by asparagine N,
In position 277: substitution of tyrosine Y by tryptophan W,
In position 287: substitution of arginine R by serine S.

24. The mutated PTE enzyme according to claim 18, having at least 13 mutations, in position 45, 48, 100, 141, 153, 177, 201, 222, 238, 239, 242, 277 and 287 in particular of sequence SED ID NO: 8, in which the at least 13 mutations are as follows:
In position 45: substitution of lysine K by alanine A,
In position 48: substitution of alanine A by methionine M,
In position 100: substitution of phenylalanine F by glutamic acid E,
In position 141: substitution of threonine T by asparagine N,
In position 153: substitution of lysine K by arginine R,
In position 177: substitution of glycine G by aspartic acid D,
In position 201: substitution of aspartic acid D by glycine G,
In position 222: substitution of histidine H by glycine G,
In position 238: substitution of alanine A by serine S,
In position 239: substitution of leucine L by tryptophan W,
In position 242: substitution of isoleucine I by asparagine N,
In position 277: substitution of tyrosine Y by tryptophan W,
In position 287: substitution of arginine R by serine S.

25. The mutated PTE enzyme according to claim 18, having at least 14 mutations, in position 45, 48, 74, 100, 141, 153, 177, 201, 222, 238, 239, 242, 277 and 287 in particular of sequence SED ID NO: 9, wherein the at least 14 mutations are as follows:

In position 45: substitution of lysine K by alanine A,

In position 48: substitution of alanine A by methionine M,

In position 74: substitution of isoleucine I by alanine A,

In position 100: substitution of phenylalanine F by glutamic acid E,

In position 141: substitution of threonine T by asparagine N,

In position 153: substitution of lysine K by arginine R,

In position 177: substitution of glycine G by aspartic acid D,

In position 201: substitution of aspartic acid D by glycine G,

In position 222: substitution of histidine H by glycine G,

In position 238: substitution of alanine A by serine S,

In position 239: substitution of leucine L by tryptophan W,

In position 242: substitution of isoleucine I by asparagine N,

In position 277: substitution of tyrosine Y by tryptophan W,

In position 287: substitution of arginine R by serine S.

* * * * *